United States Patent
Sos

(10) Patent No.: US 10,231,751 B2
(45) Date of Patent: *Mar. 19, 2019

(54) THROMBUS REMOVAL AND INTRAVASCULAR DISTAL EMBOLIC PROTECTION DEVICE

(71) Applicant: Thomas A. Sos, New York, NY (US)

(72) Inventor: Thomas A. Sos, New York, NY (US)

(*) Notice: Subject to any disclaimer, the term of this patent is extended or adjusted under 35 U.S.C. 154(b) by 262 days.

This patent is subject to a terminal disclaimer.

(21) Appl. No.: 15/226,223

(22) Filed: Aug. 2, 2016

(65) Prior Publication Data

US 2016/0367285 A1    Dec. 22, 2016

Related U.S. Application Data

(63) Continuation-in-part of application No. 14/550,289, filed on Nov. 21, 2014, now Pat. No. 9,439,664, (Continued)

(51) Int. Cl.
*A61B 17/221* (2006.01)
*A61B 17/3207* (2006.01)
(Continued)

(52) U.S. Cl.
CPC .... *A61B 17/320725* (2013.01); *A61B 17/221* (2013.01); *A61B 17/22032* (2013.01);
(Continued)

(58) Field of Classification Search
CPC .............. A61B 17/22; A61B 17/22031; A61B 17/22032; A61B 17/221; A61B 17/3207;
(Continued)

(56) References Cited

U.S. PATENT DOCUMENTS

| 5,662,671 A | 9/1997 | Barbut et al. |
| 5,759,173 A | 6/1998 | Preissman et al. |

(Continued)

FOREIGN PATENT DOCUMENTS

| EP | 3017775 A1 | 5/2016 |
| JP | S60135039 A | 7/1985 |

(Continued)

OTHER PUBLICATIONS

Extended European search report and opinion dated Jan. 11, 2017 for EP Application No. 14804362.

(Continued)

*Primary Examiner* — Ryan J. Severson
(74) *Attorney, Agent, or Firm* — Wilson Sonsini Goodrich & Rosati

(57) ABSTRACT

A clot extraction catheter comprises a tubular mesh, a rim attached to the tubular mesh proximal end, control wires, an inner sheath, a clot macerator advancable from the inner sheath, and an outer sheath advancable over the guidewire channel and inner sheath. To extract a clot, the catheter is advanced through the clot. The inner sheath is retracted, allowing the rim and the tubular mesh to expand as well as exposing the clot macerator. The tubular mesh is retracted to capture the clot, constrained proximally by the distal portion of the inner sheath, and retracted with the inner sheath into the outer sheath. The clot macerator breaks apart large clots as the clot is captured, and the tubular mesh is retracted over the clot macerator. The control wires may be manipulated to control the angle of the rim, thereby facilitating clot capture and retraction of the tubular mesh.

18 Claims, 35 Drawing Sheets

Related U.S. Application Data which is a continuation-in-part of application No. 14/289,027, filed on May 28, 2014, now Pat. No. 9,427,252.

(60) Provisional application No. 62/246,481, filed on Oct. 26, 2015, provisional application No. 62/298,391, filed on Feb. 22, 2016, provisional application No. 61/828,264, filed on May 29, 2013.

(51) Int. Cl.
  *A61F 2/01* (2006.01)
  *A61B 17/22* (2006.01)
  *A61B 17/00* (2006.01)

(52) U.S. Cl.
  CPC ...... *A61B 17/320758* (2013.01); *A61F 2/013* (2013.01); *A61B 2017/00778* (2013.01); *A61B 2017/2212* (2013.01); *A61B 2017/22038* (2013.01); *A61B 2017/22042* (2013.01); *A61B 2017/22049* (2013.01); *A61B 2017/22065* (2013.01); *A61B 2017/22094* (2013.01); *A61B 2017/320716* (2013.01); *A61B 2017/320733* (2013.01); *A61B 2017/320775* (2013.01); *A61F 2002/016* (2013.01)

(58) Field of Classification Search
  CPC .... A61B 17/320725; A61B 17/320758; A61B 2017/00778; A61B 2017/22034; A61B 2017/22035; A61B 2017/22038; A61B 2017/22051; A61B 2017/22072; A61B 2017/22078; A61B 2017/22081; A61B 2017/22094; A61B 2017/2212; A61B 2017/22015; A61B 2017/320716; A61B 2017/320775; A61F 2/013
  See application file for complete search history.

(56) References Cited

U.S. PATENT DOCUMENTS

| | | | |
|---|---|---|---|
| 5,848,964 | A | 12/1998 | Samuels |
| 5,895,399 | A | 4/1999 | Barbut et al. |
| 5,947,995 | A | 9/1999 | Samuels |
| 5,993,469 | A | 11/1999 | McKenzie et al. |
| 5,997,557 | A | 12/1999 | Barbut et al. |
| 6,010,522 | A | 1/2000 | Barbut et al. |
| 6,129,739 | A | 10/2000 | Khosravi |
| 6,168,579 | B1 | 1/2001 | Tsugita |
| 6,179,851 | B1 | 1/2001 | Barbut et al. |
| 6,245,087 | B1 | 6/2001 | Addis |
| 6,309,399 | B1 | 10/2001 | Barbut et al. |
| 6,391,044 | B1 | 5/2002 | Yadav et al. |
| 6,428,552 | B1 | 8/2002 | Sparks |
| 6,494,895 | B2 | 12/2002 | Addis |
| 6,530,939 | B1 | 3/2003 | Hopkins et al. |
| 6,569,184 | B2 * | 5/2003 | Huter ............ A61F 2/013 606/200 |
| 6,620,148 | B1 | 9/2003 | Tsugita |
| 6,620,182 | B1 | 9/2003 | Khosravi et al. |
| 6,652,548 | B2 * | 11/2003 | Evans ............ A61B 17/221 606/159 |
| 6,682,543 | B2 | 1/2004 | Barbut et al. |
| 6,695,865 | B2 | 2/2004 | Boyle et al. |
| 6,755,813 | B2 | 6/2004 | Ouriel et al. |
| 6,755,846 | B1 | 6/2004 | Yadav |
| 6,824,545 | B2 | 11/2004 | Sepetka et al. |
| 6,893,431 | B2 | 5/2005 | Naimark et al. |
| 6,918,921 | B2 | 7/2005 | Brady et al. |
| 6,945,977 | B2 * | 9/2005 | Demarais ....... A61B 17/320725 606/128 |
| 6,964,672 | B2 | 11/2005 | Brady et al. |
| 6,974,469 | B2 | 12/2005 | Broome et al. |
| 7,014,647 | B2 | 3/2006 | Brady et al. |
| 7,037,320 | B2 | 5/2006 | Brady et al. |
| 7,097,440 | B2 | 8/2006 | Papp et al. |
| 7,306,618 | B2 | 12/2007 | Demond et al. |
| 7,311,661 | B2 | 12/2007 | Heinrich |
| 7,320,697 | B2 * | 1/2008 | Demond ............ A61B 17/221 606/200 |
| 7,479,153 | B2 | 1/2009 | Belef et al. |
| 7,481,788 | B2 | 1/2009 | Naimark et al. |
| 7,608,087 | B1 | 10/2009 | Addis |
| 7,731,722 | B2 | 6/2010 | Lavelle et al. |
| 7,799,051 | B2 | 9/2010 | Brady et al. |
| 7,927,349 | B2 | 4/2011 | Brady et al. |
| 7,938,798 | B2 | 5/2011 | Naimark et al. |
| 7,976,560 | B2 | 7/2011 | Denison et al. |
| 7,993,363 | B2 | 8/2011 | Demond et al. |
| 8,002,790 | B2 | 8/2011 | Brady et al. |
| 8,083,762 | B2 | 12/2011 | Kusleika et al. |
| 8,114,115 | B2 | 2/2012 | Brady et al. |
| 8,216,269 | B2 * | 7/2012 | Magnuson ............ A61F 2/013 606/200 |
| 8,377,092 | B2 | 2/2013 | Magnuson |
| 8,444,665 | B2 | 5/2013 | Tsugita |
| 8,486,105 | B2 | 7/2013 | Demond et al. |
| 8,591,540 | B2 * | 11/2013 | Boyle ............ A61F 2/013 606/200 |
| 8,777,976 | B2 * | 7/2014 | Brady ............ A61B 17/22031 606/127 |
| 8,956,385 | B2 * | 2/2015 | Frimerman ............ A61F 2/013 606/200 |
| 9,017,294 | B2 * | 4/2015 | McGuckin, Jr. ....... A61B 17/22 604/247 |
| 9,220,522 | B2 * | 12/2015 | Fulkerson ............ A61B 17/221 |
| 9,358,022 | B2 * | 6/2016 | Morsi ................ A61B 17/221 |
| 9,427,252 | B2 | 8/2016 | Sos et al. |
| 9,439,664 | B2 | 9/2016 | Sos et al. |
| 9,492,264 | B2 * | 11/2016 | Fifer ............ A61F 2/013 |
| 2001/0016755 | A1 | 8/2001 | Addis |
| 2002/0002384 | A1 * | 1/2002 | Gilson ............ A61F 2/01 606/200 |
| 2002/0010487 | A1 | 1/2002 | Evans et al. |
| 2002/0026213 | A1 * | 2/2002 | Gilson ............ A61F 2/01 606/200 |
| 2002/0072764 | A1 | 6/2002 | Sepetka et al. |
| 2002/0082639 | A1 | 6/2002 | Broome et al. |
| 2002/0095171 | A1 | 7/2002 | Belef |
| 2002/0099397 | A1 | 7/2002 | Sparks |
| 2002/0120287 | A1 | 8/2002 | Huter |
| 2002/0123761 | A1 | 9/2002 | Barbut et al. |
| 2002/0133191 | A1 | 9/2002 | Khosravi et al. |
| 2002/0161393 | A1 | 10/2002 | Demond et al. |
| 2002/0165576 | A1 | 11/2002 | Boyle et al. |
| 2003/0009189 | A1 * | 1/2003 | Gilson ............ A61F 2/01 606/200 |
| 2003/0073979 | A1 | 4/2003 | Naimark et al. |
| 2003/0097114 | A1 | 5/2003 | Ouriel et al. |
| 2003/0130684 | A1 | 7/2003 | Brady et al. |
| 2003/0144687 | A1 | 7/2003 | Brady et al. |
| 2003/0144688 | A1 | 7/2003 | Brady et al. |
| 2003/0144689 | A1 | 7/2003 | Brady et al. |
| 2003/0208228 | A1 * | 11/2003 | Gilson ............ A61F 2/01 606/200 |
| 2004/0006370 | A1 | 1/2004 | Tsugita |
| 2004/0034385 | A1 * | 2/2004 | Gilson ............ A61F 2/01 606/200 |
| 2004/0039411 | A1 * | 2/2004 | Gilson ............ A61F 2/01 606/200 |
| 2004/0073198 | A1 * | 4/2004 | Gilson ............ A61F 2/01 606/1 |
| 2004/0082962 | A1 | 4/2004 | Demarais et al. |
| 2004/0098032 | A1 | 5/2004 | Papp et al. |
| 2004/0116960 | A1 | 6/2004 | Demond et al. |
| 2005/0004595 | A1 | 1/2005 | Boyle et al. |
| 2005/0043756 | A1 | 2/2005 | Lavelle et al. |
| 2005/0049619 | A1 | 3/2005 | Sepetka et al. |
| 2005/0165280 | A1 | 7/2005 | Heinrich |
| 2005/0177106 | A1 | 8/2005 | Naimark et al. |
| 2005/0209634 | A1 | 9/2005 | Brady et al. |

(56) References Cited

U.S. PATENT DOCUMENTS

| | | |
|---|---|---|
| 2006/0122644 A1 | 6/2006 | Brady et al. |
| 2006/0122645 A1 | 6/2006 | Brady et al. |
| 2006/0229658 A1 | 10/2006 | Stivland |
| 2006/0241681 A1 | 10/2006 | Brady et al. |
| 2007/0100373 A1 | 5/2007 | Magnuson et al. |
| 2007/0208374 A1 | 9/2007 | Boyle et al. |
| 2007/0233179 A1 | 10/2007 | Brady et al. |
| 2007/0233180 A1 | 10/2007 | Brady et al. |
| 2007/0233183 A1 | 10/2007 | Brady et al. |
| 2008/0058860 A1 | 3/2008 | Demond et al. |
| 2008/0109031 A1 | 5/2008 | Sepetka et al. |
| 2009/0105722 A1 | 4/2009 | Fulkerson et al. |
| 2009/0131882 A1 | 5/2009 | Naimark et al. |
| 2010/0168785 A1 | 7/2010 | Parker |
| 2011/0125181 A1 | 5/2011 | Brady et al. |
| 2011/0137334 A1 | 6/2011 | Anderson et al. |
| 2011/0160741 A1 | 6/2011 | Asano et al. |
| 2011/0166586 A1 | 7/2011 | Sepetka et al. |
| 2011/0264135 A1 | 10/2011 | Demond et al. |
| 2012/0172915 A1 | 7/2012 | Fifer et al. |
| 2012/0330346 A1 | 12/2012 | Frimerman |
| 2012/0330350 A1 | 12/2012 | Jones et al. |
| 2013/0184739 A1 | 7/2013 | Brady et al. |
| 2013/0190789 A1 | 7/2013 | McGuckin, Jr. et al. |
| 2013/0253467 A1 | 9/2013 | Gianotti et al. |
| 2013/0310803 A1 | 11/2013 | Morsi |
| 2014/0052103 A1 | 2/2014 | Cully et al. |
| 2015/0025555 A1 | 1/2015 | Sos |
| 2015/0297251 A1 | 10/2015 | Sos et al. |
| 2016/0367285 A1* | 12/2016 | Sos ................. A61B 17/22032 |

FOREIGN PATENT DOCUMENTS

| | | |
|---|---|---|
| JP | 2003530911 A | 10/2003 |
| JP | 2004531346 A | 10/2004 |
| JP | 2004535843 A | 12/2004 |
| JP | 2006087473 A | 4/2006 |
| JP | 2008535588 A | 9/2008 |
| WO | WO-2007035885 A2 | 3/2007 |

OTHER PUBLICATIONS

International search report and written opinion dated Feb. 24, 2015 for PCT Application No. US2014/066925.
International search report and written opinion dated Oct. 20, 2016 for PCT/US2016/045206.
International search report and written opinion dated Oct. 22, 2014 for PCT/US2014/039843.
Notice of allowance dated May 2, 2016 for U.S. Appl. No. 14/550,289.
Notice of allowance dated May 4, 2016 for U.S. Appl. No. 14/289,027.
Office action dated Apr. 8, 2016 for U.S. Appl. No. 14/289,027.
Office action dated Dec. 31, 2015 for U.S. Appl. No. 14/550,289.

* cited by examiner

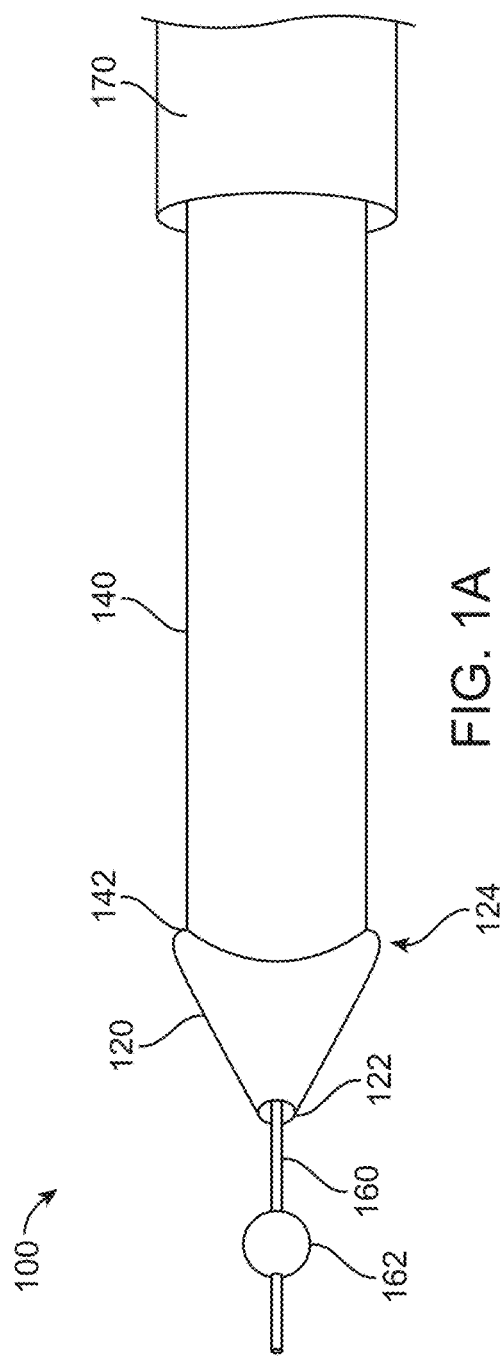
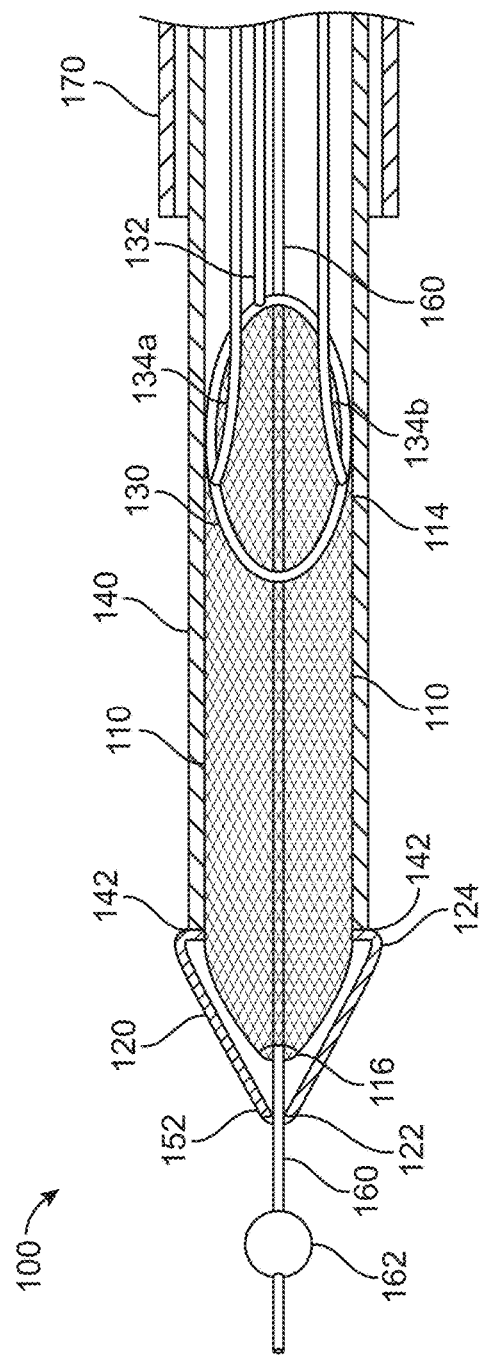

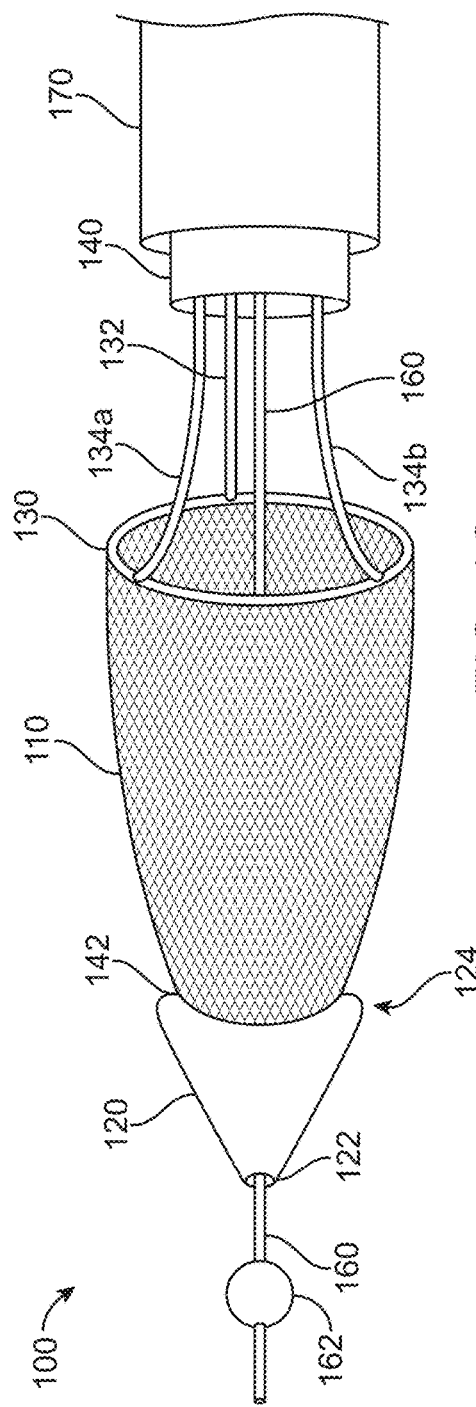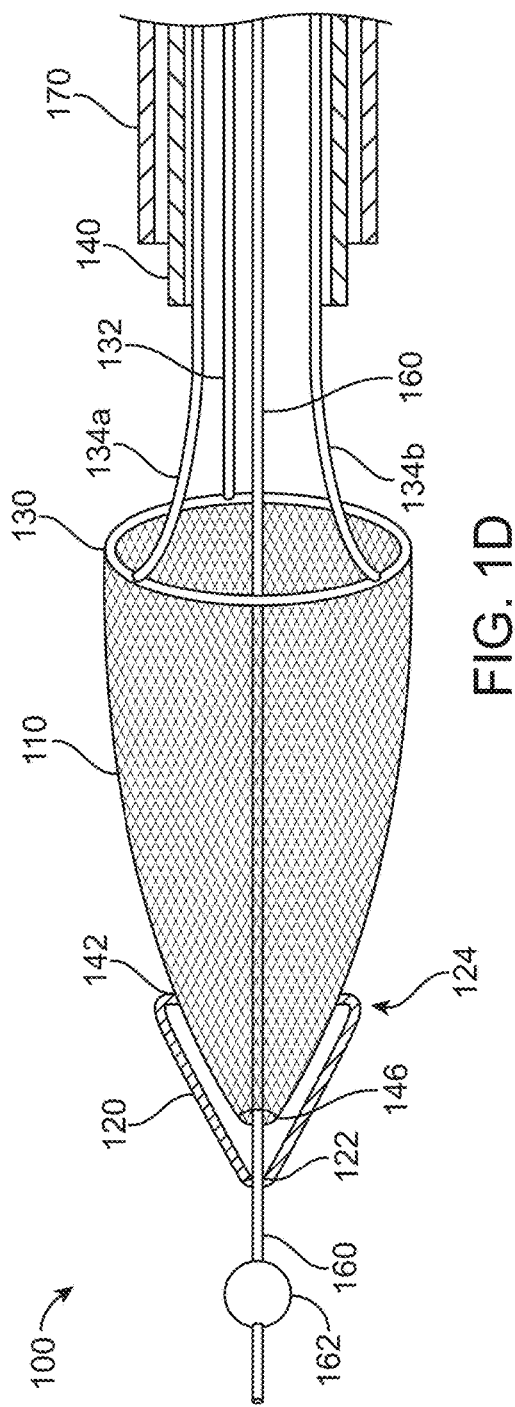

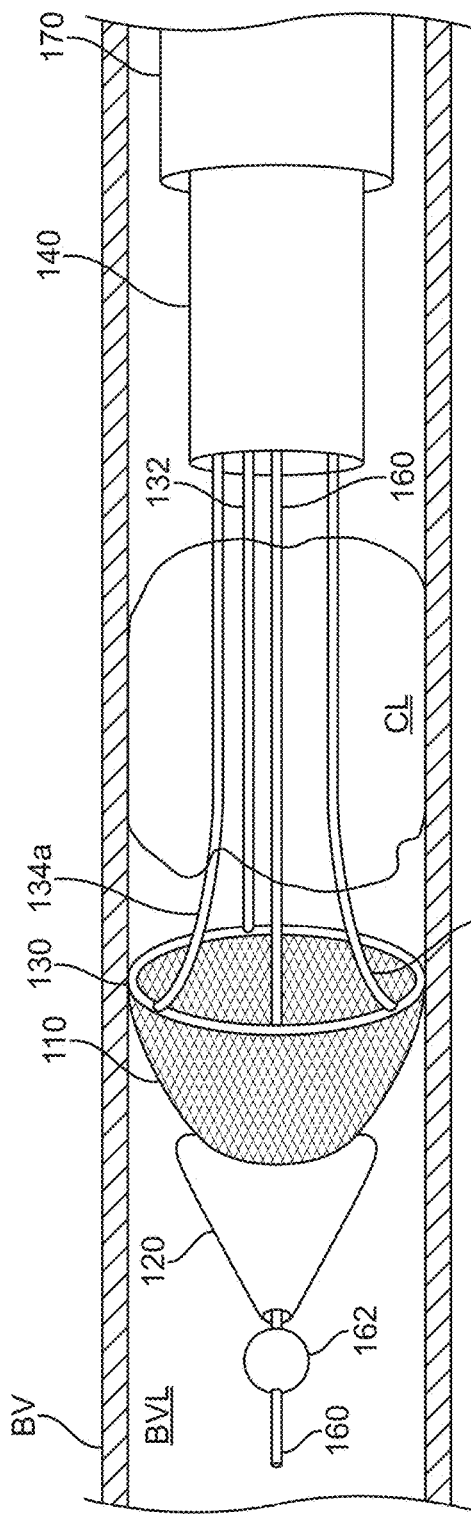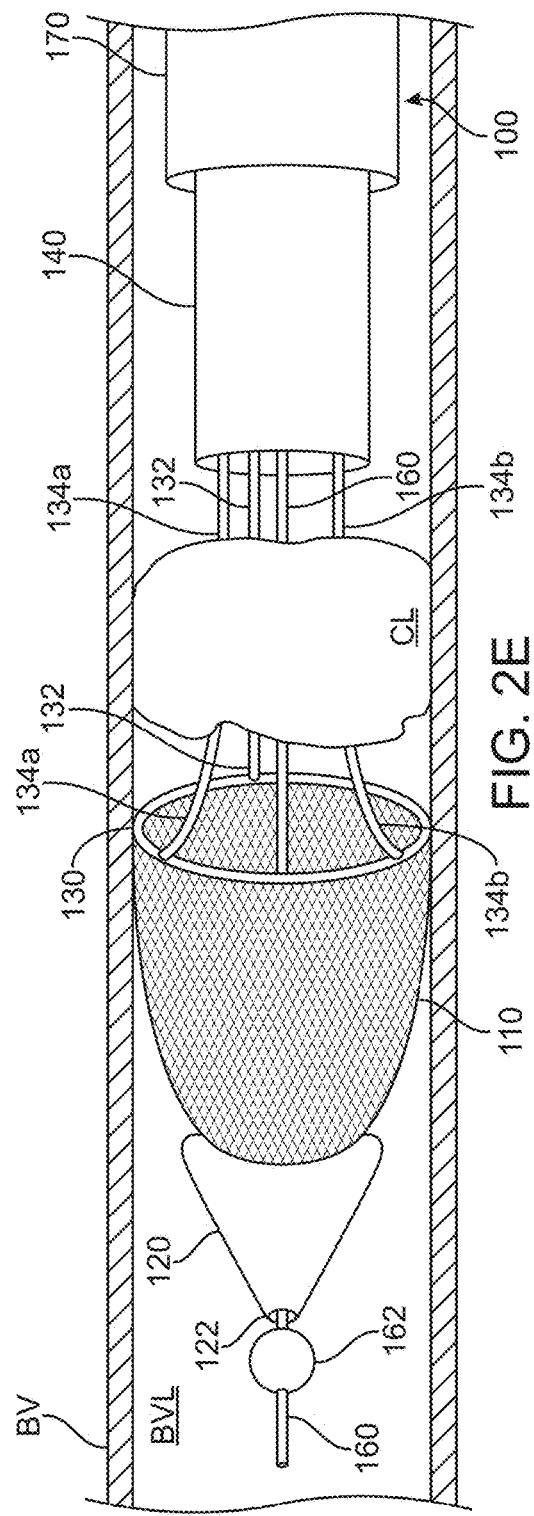

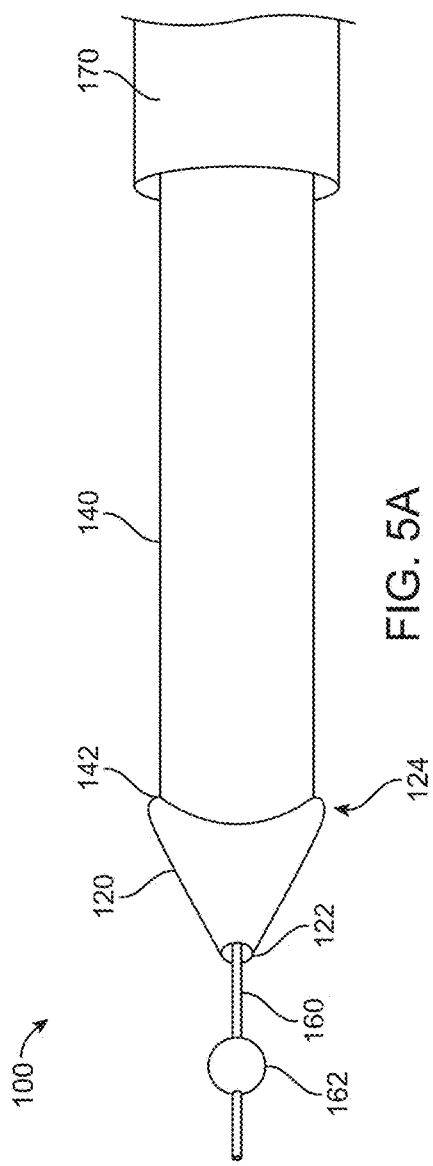
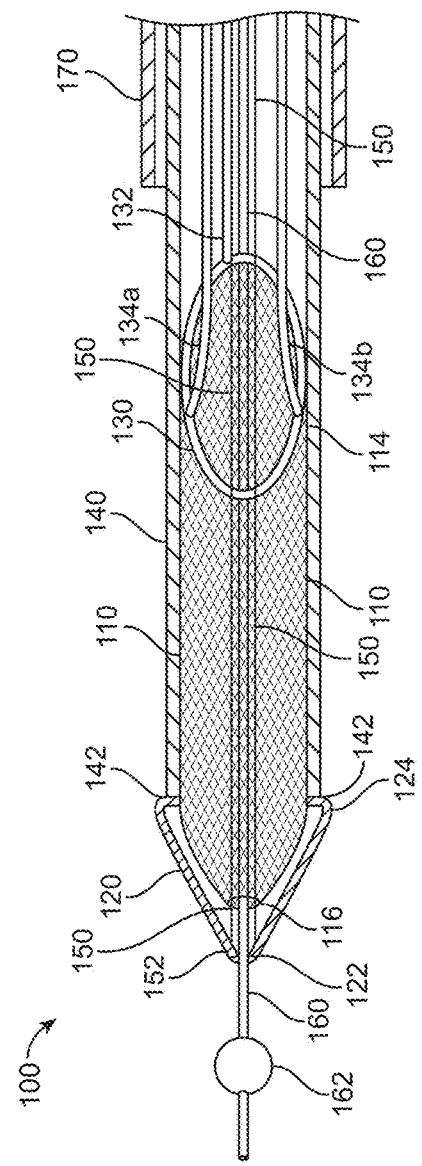
FIG. 5A
FIG. 5B

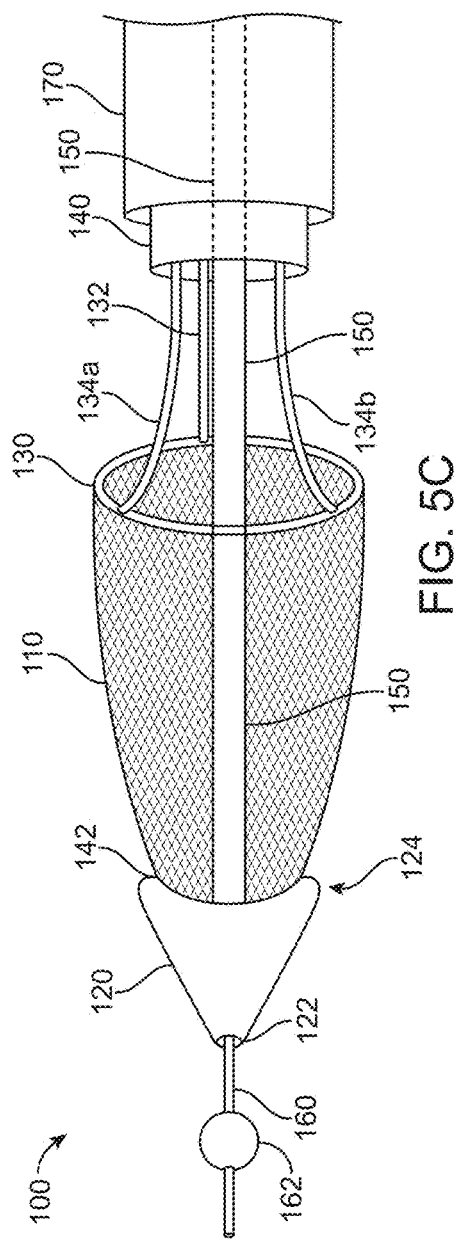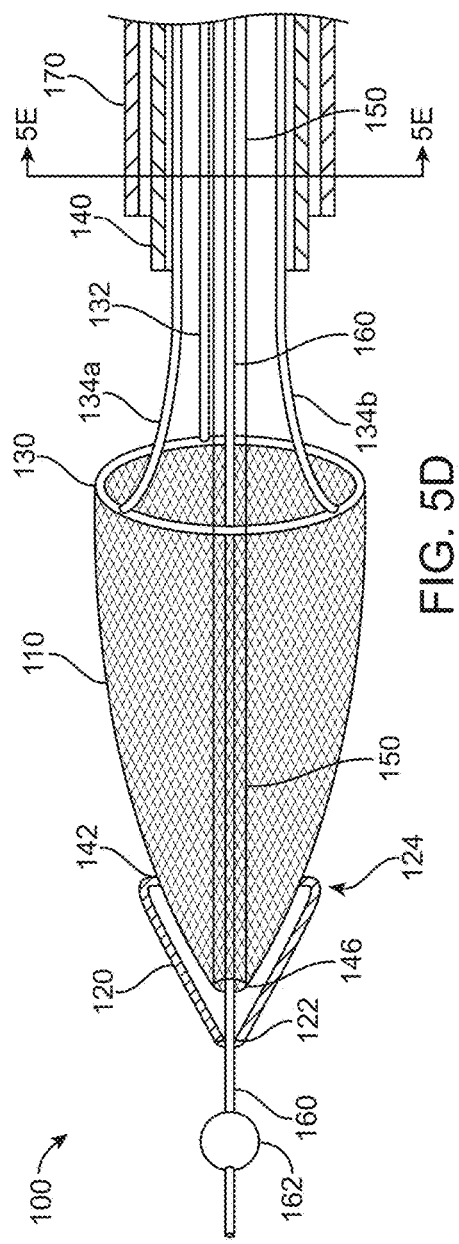

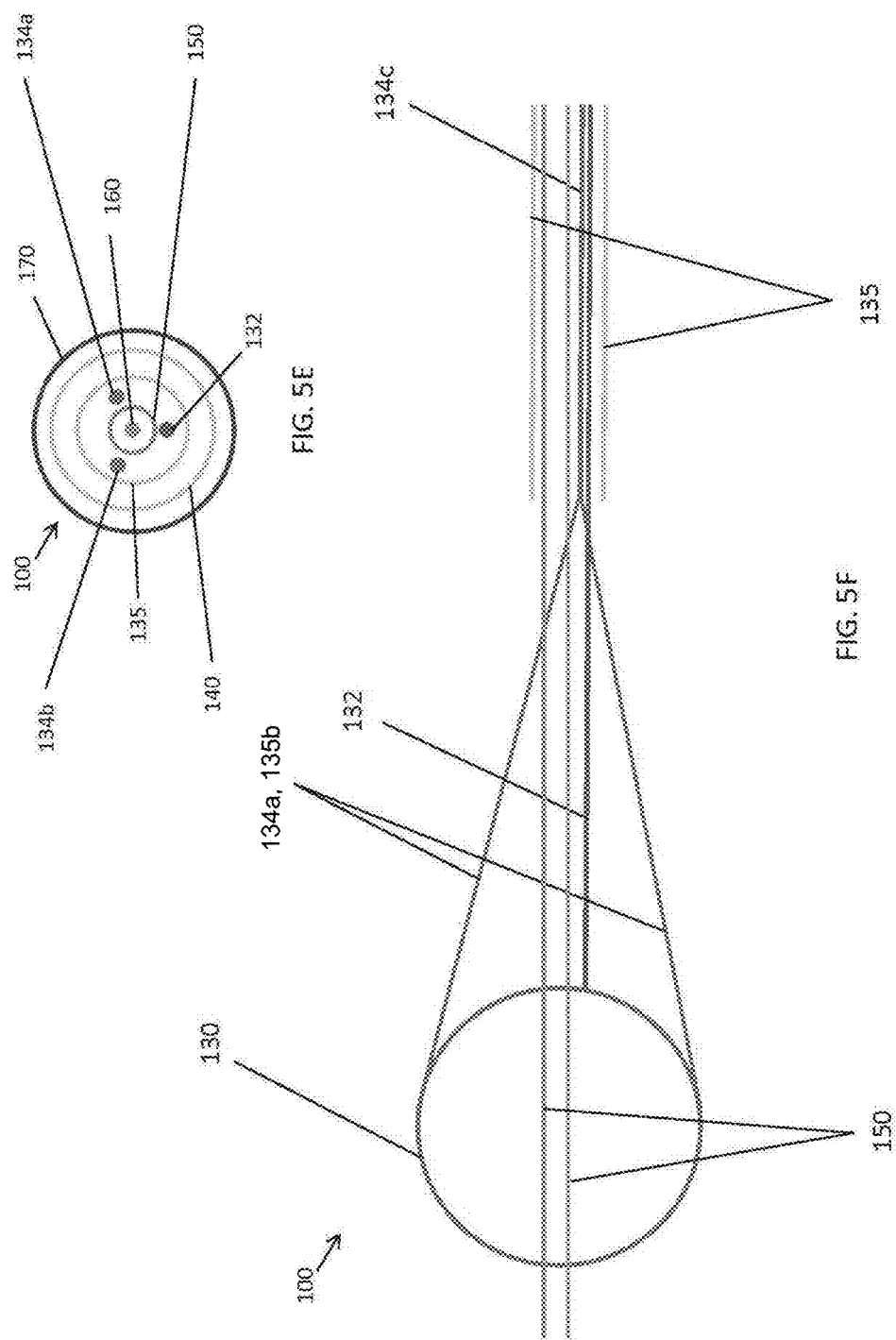

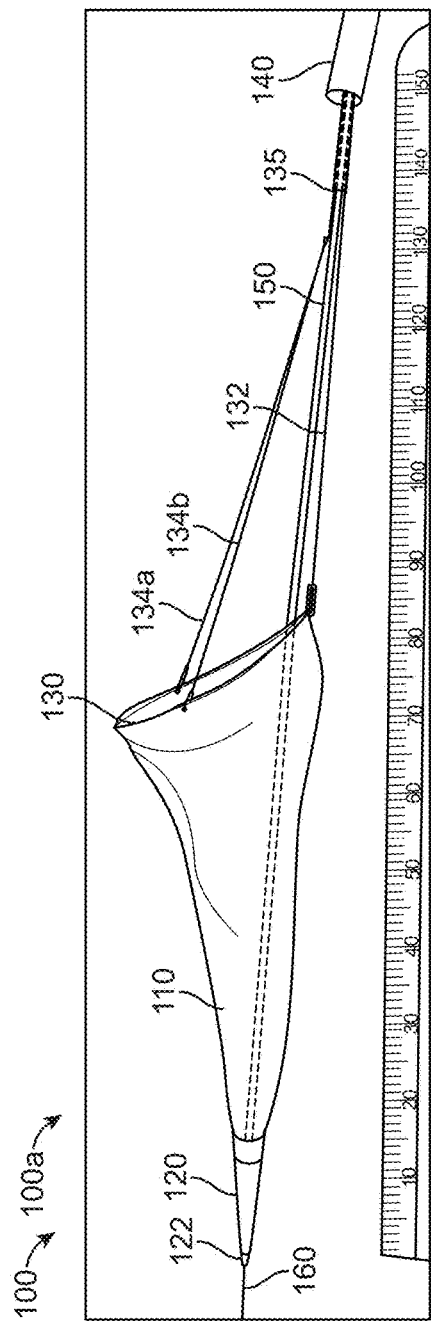
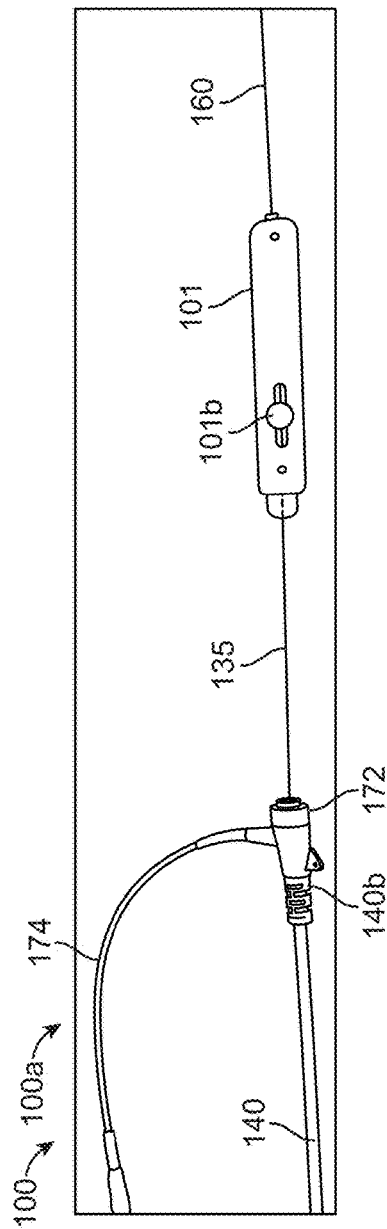
FIG. 6A
FIG. 6B

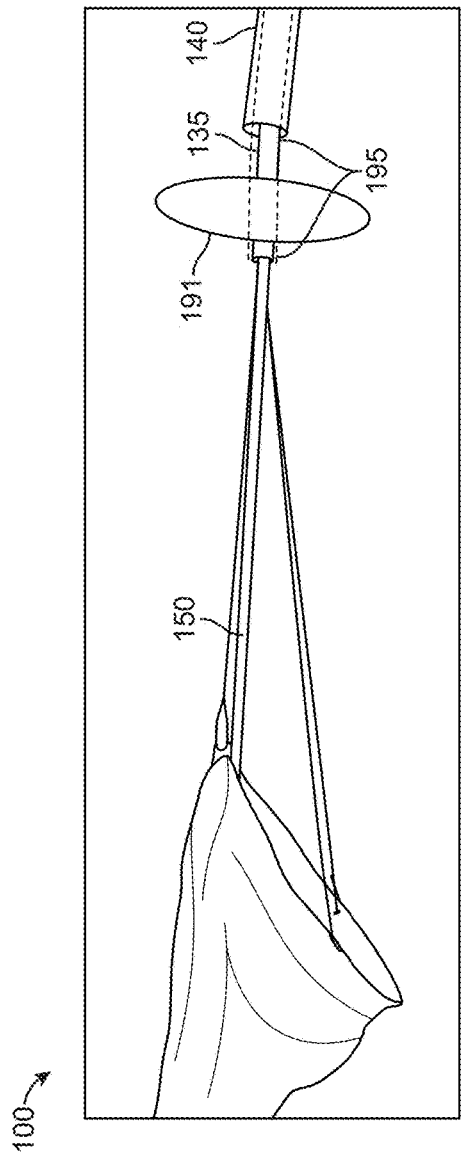
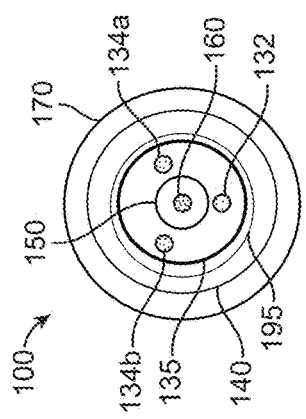
FIG. 7A
FIG. 7B

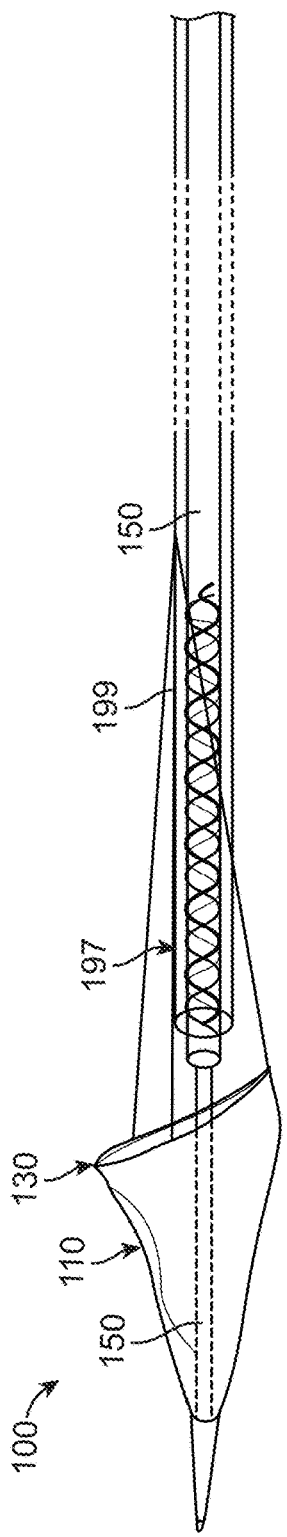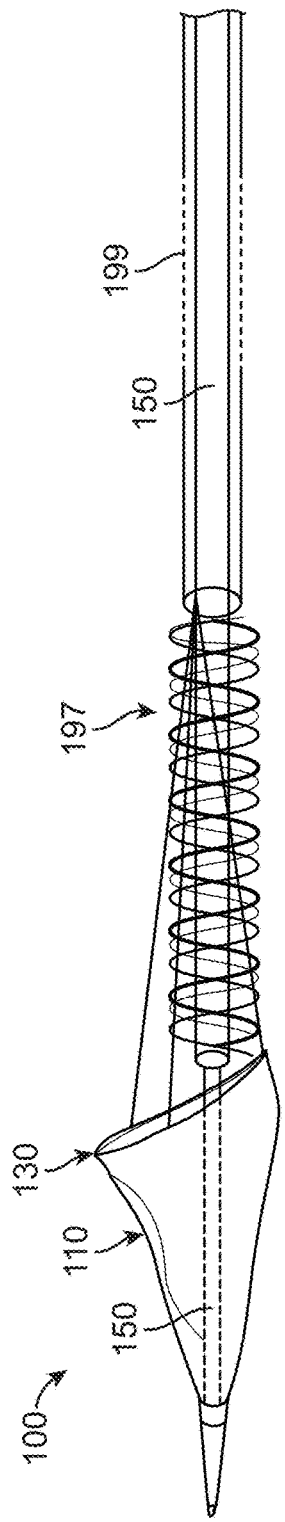
FIG. 10A
FIG. 10B

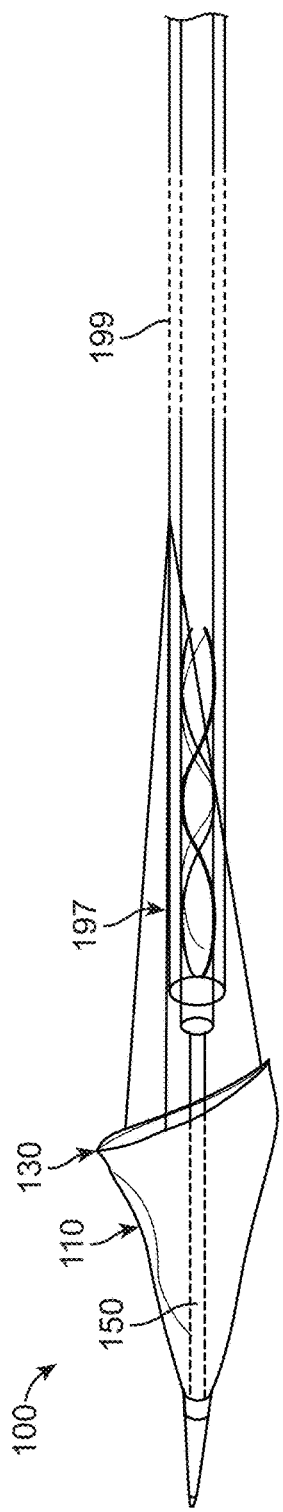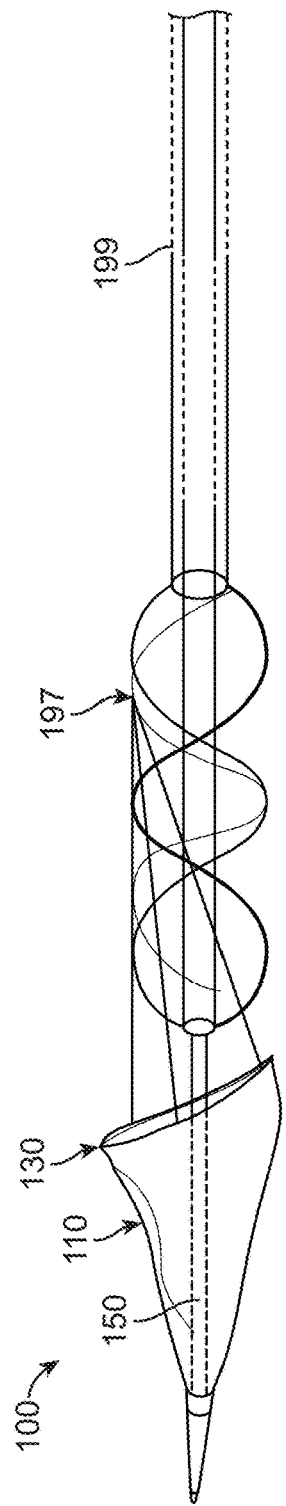

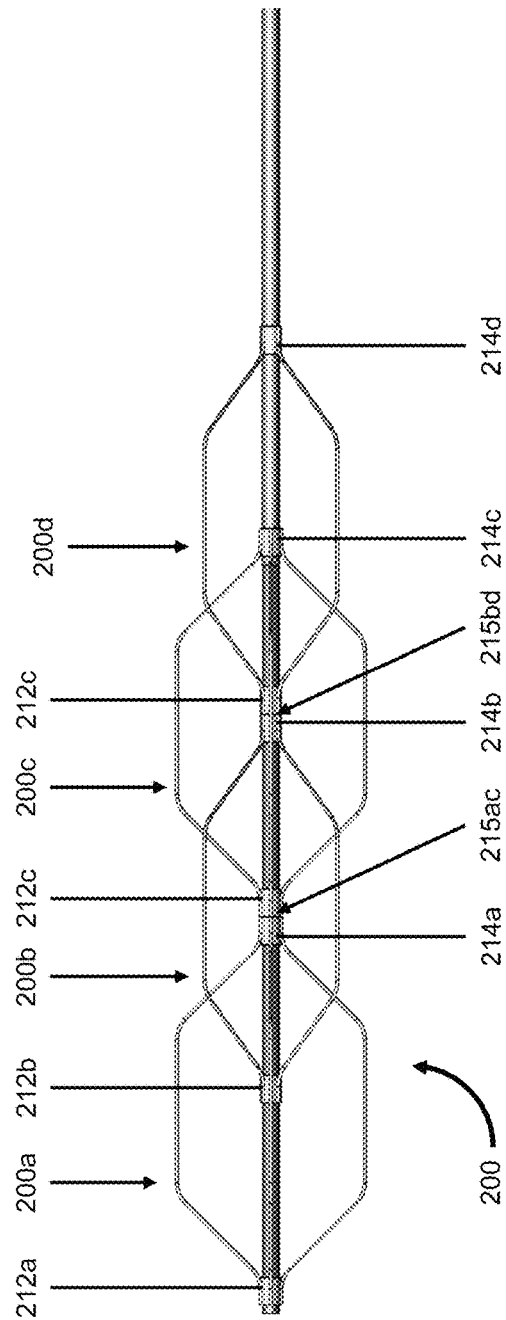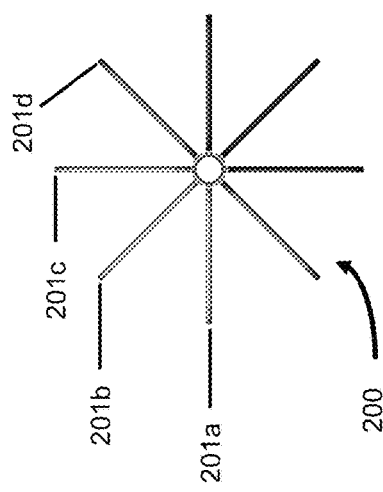

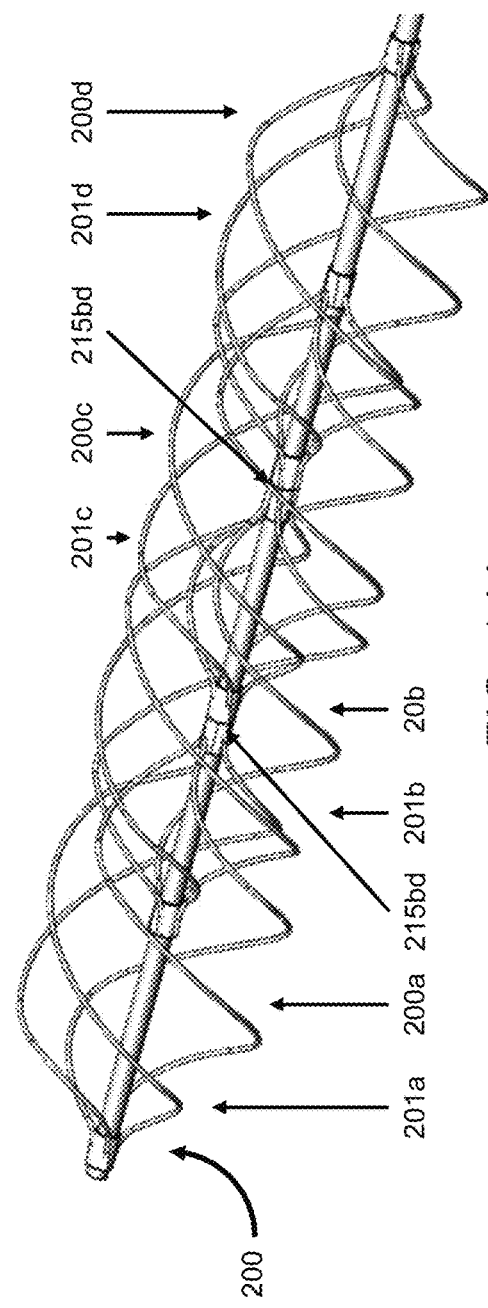
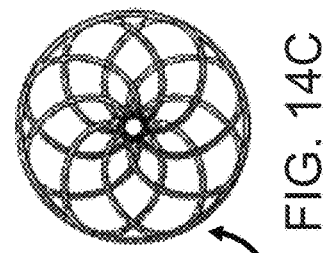
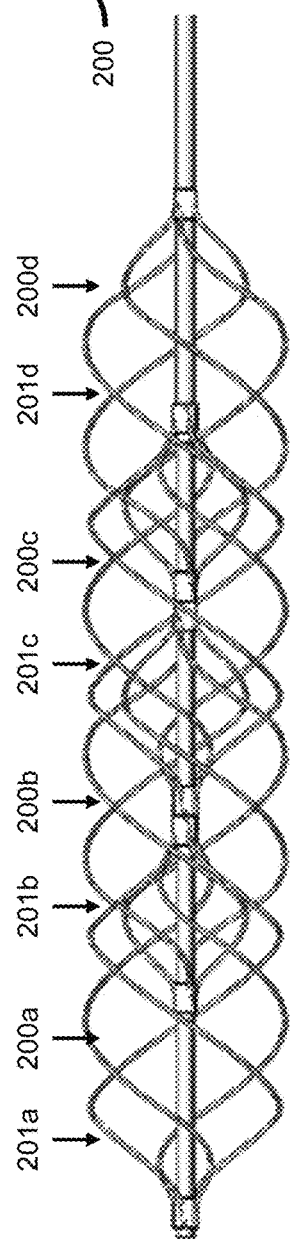
FIG. 14A
FIG. 14B
FIG. 14C

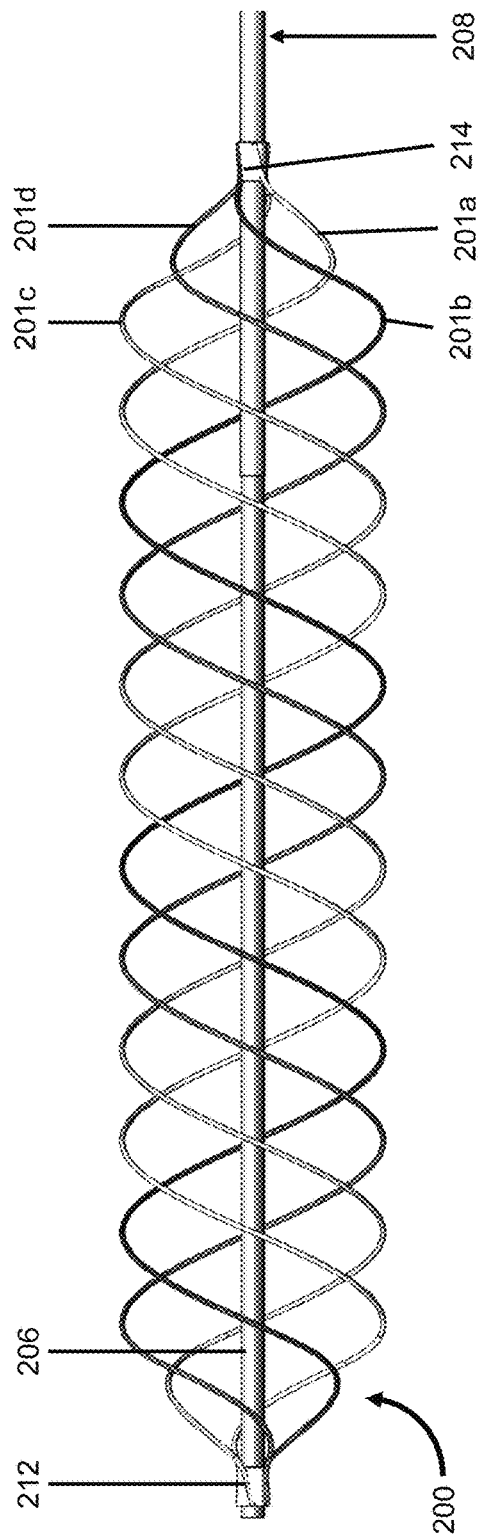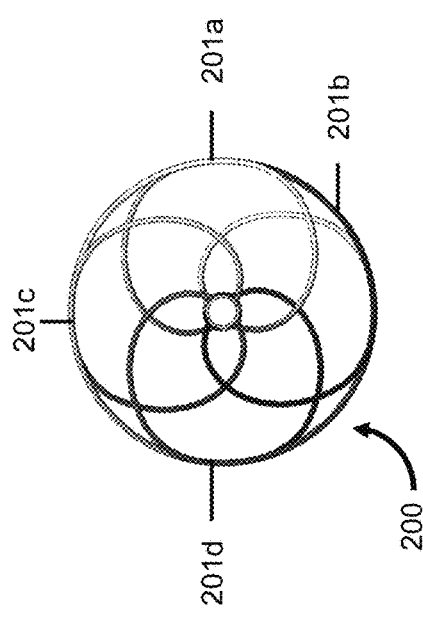
FIG. 15A
FIG. 15B

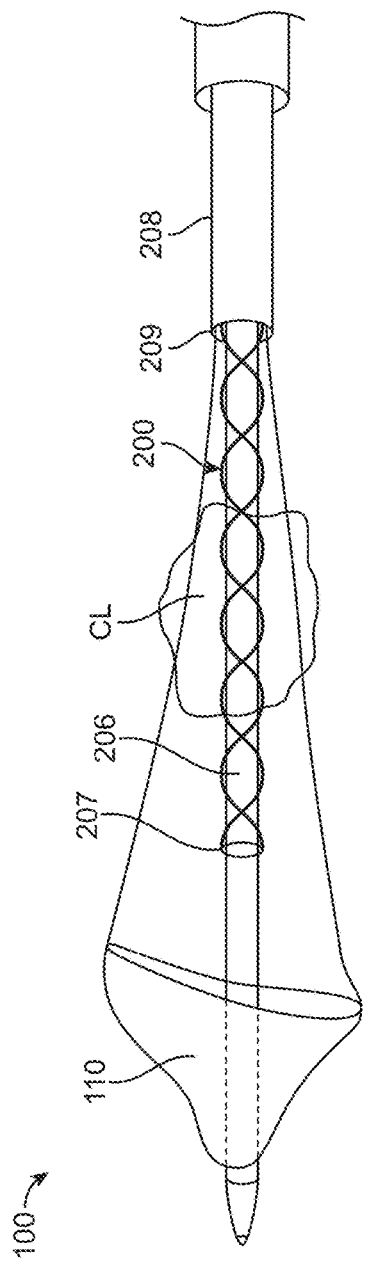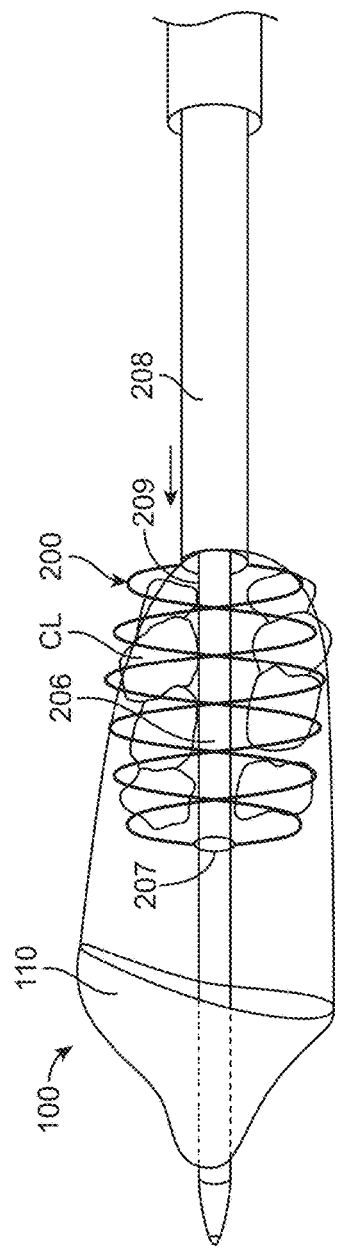
FIG. 20A
FIG. 20B

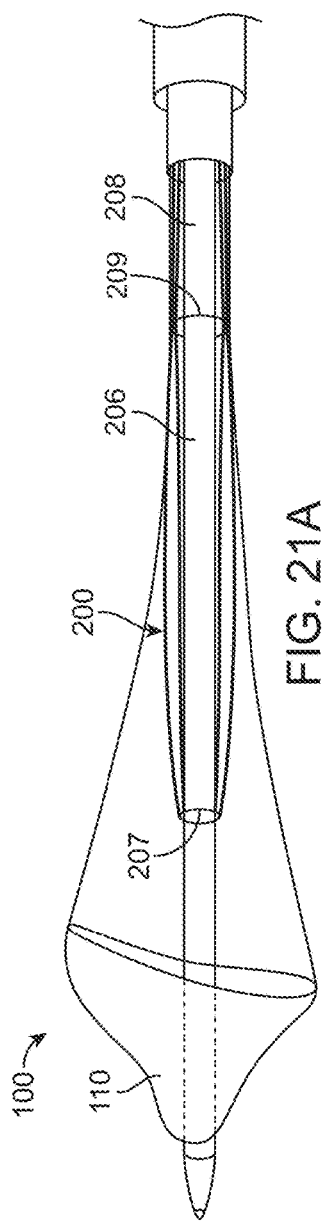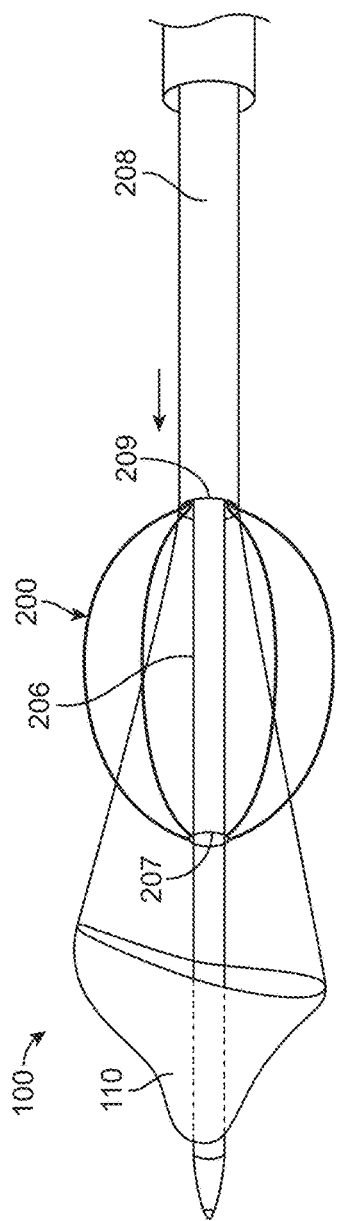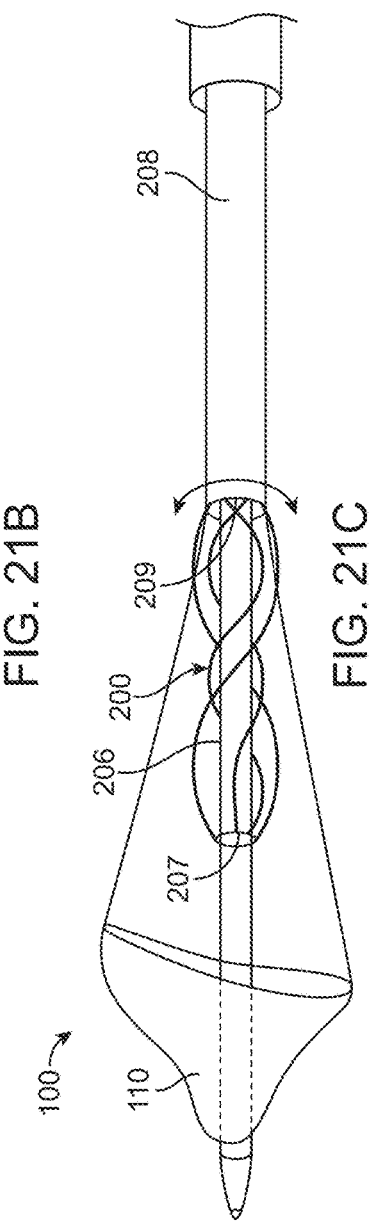

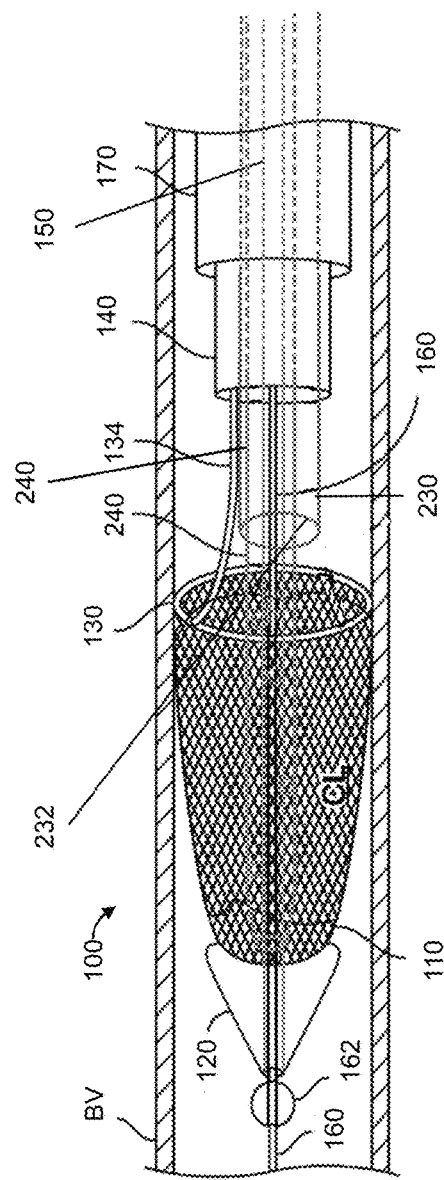
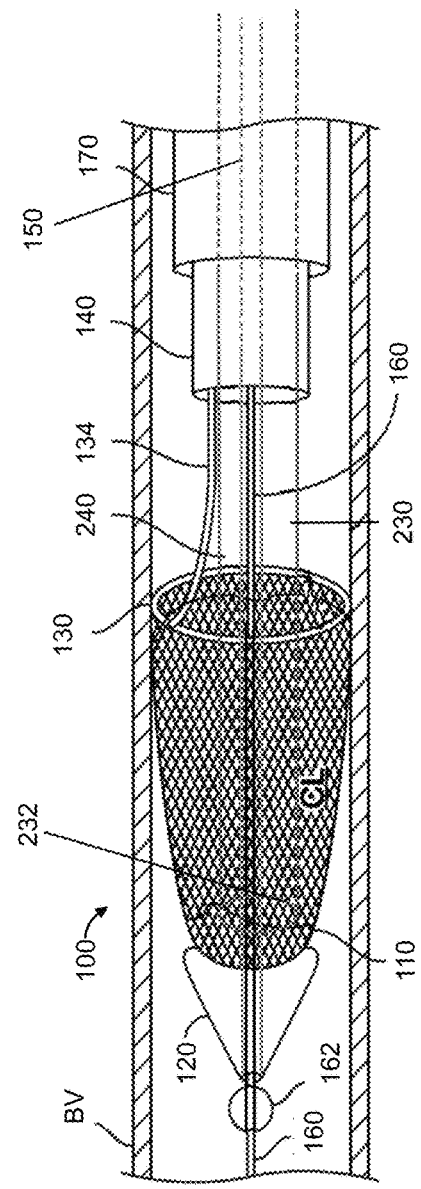

THROMBUS REMOVAL AND INTRAVASCULAR DISTAL EMBOLIC PROTECTION DEVICE

CROSS-REFERENCE

This application claims the benefit of U.S. Provisional Application No. 62/246,481, filed Oct. 26, 2015, and U.S. Provisional Application No. 62/298,391, filed Feb. 22, 2016, which applications are incorporated herein by reference; and, this application is also a continuation-in-part of U.S. patent application Ser. No. 14/550,289, filed Nov. 21, 2014, which is a continuation-in-part of U.S. patent application Ser. No. 14/289,027, filed May 28, 2014, which claims the benefit of U.S. Provisional Application No. 61/828,264, filed May 29, 2013, the full disclosures of which are incorporated herein by reference.

BACKGROUND

The present disclosure generally relates to medical devices, systems, and methods. In particular, the present disclosure generally relates to the removal of intravascular or intracavitary thrombus or other material which may frequently require removal to restore blood flow or other normal functionality of the organ system affected.

Typically, blood clot or emboli to the pulmonary arteries of the lung, the brain, the peripheral arteries of the extremities, in the venous system, or in dialysis access vessels are potentially life and/or limb threatening conditions. These clots are typically cleared when medically indicated by either pharmacological (thrombolytic and/or anticoagulant drugs) or mechanical means or a combination of the two. Thrombolytic drugs typically require several hours to days to accomplish dissolving these clots. Frequently, there is not sufficient "warm" ischemic time for the target organ to permit such a long time to reperfusion. Thrombolytic drugs also have an approximately 5% incidence of major complications such as hemorrhage and stroke. Currently available mechanical devices may not be effective in the presence of large volumes of thrombus or may have a very large diameter and may be stiff. Thus, these devices may be difficult or impossible to advance into curved and tortuous vessels such as the pulmonary arteries. The "Hydrolyzer" devices available in the marketplace may break up a clot and suction the resulting particles out, but may infuse large volumes of fluid as part of their action. Such infusion may be physiologically difficult to handle for the patient. Other devices, like "AngioVac" may require a miniature veno-venous cardiovascular bypass to allow filtering out of the suctioned thrombus and return of the cleared blood to the patient. Most of these devices may also hemolyze blood, which may result in damage to the kidneys and may also cause distal emboli.

For these reasons, emergency open surgical thrombectomy, which in itself may have a high mortality and morbidity, is often employed as a last resort, especially for large pulmonary emboli. There are therefore needs for devices which can rapidly and safely extract large volumes of blood clot or other materials with little or no adjuvant use of thrombolytic drugs. Such devices may be used during intravascular interventions to prevent distal embolization by capture of blood clots or atheromatous material.

SUMMARY

The present disclosure provides medical devices, systems, and methods for the removal of intravascular or intracavitary thrombus or other material.

Aspects of the present disclosure provide clot extraction catheters. A clot extraction catheter may comprise an expandable tubular mesh, a tapered tip, a self-expanding rim, at least three control wires, and an inner sheath. The expandable tubular mesh may have a distal end and a proximal end. The expandable tubular mesh may have an expanded configuration and a constrained configuration. The tapered tip may be fixed to the distal end of the expandable tubular mesh. The self-expanding rim may be attached to the proximal end of the expandable tubular mesh. The self-expanding rim may have an unconstrained diameter which is greater than a width of the proximal end of the tapered tip. The control wires may be attached to the self-expanding rim. The inner sheath may be advancable over the control wires to constrain at least a portion of the self-expanding rim and at least a portion of the tubular mesh within a lumen of the inner sheath. The control wires can be manipulated to control the angle of the self-expanding rim relative to the longitudinal axis of the inner sheath when the self-expanding rim is unconstrained. The self-expanding rim may be advanced past a clot, expanded, and finally retracted to capture the clot within the expandable tubular mesh. The clot extraction catheter may further comprise an outer sheath advancable over the inner sheath.

In some embodiments, an expandable element may be provided to facilitate clot capture in conjunction with the self-expanding rim. The expandable element, typically an inflatable balloon, may be mounted on a distal end of the inner sheath, on a separate pusher tube, or on a control wire sheath further described below. The pusher sheath may be axially translated to advance and retract the expandable element. The pusher sheath may be disposed within the outer sheath and possibly even within the inner sheath. Retraction of the self-expanding rim may push the clot against the expanded expandable element to urge the clot into the expandable tubular mesh. Alternatively or in combination, the expandable element may be advanced to push the clot into the expandable tubular mesh.

Referring back to the other components of the clot extraction catheter, the proximal end of the tapered tip may have a rounded lip to reduce interference as the catheter is drawn proximally through a bodily lumen or cavity.

The control wires may comprise a main wire and two chord wires. The main wire may be translatable proximally and distally. The two chord wires may be translatable proximally and distally independently from the primary wire. The wires may be independently translated proximally and/or distally to control the angle of the self-expanding rim relative to the axis of the inner sheath when the self-expanding rim is unconstrained. The two chord wires may comprise a first chord wire and a second chord wire each independently translatable proximally and distally. In some embodiments, the main control wire may be fixed and the two chord wires may be independently translatable proximally and distally. The control wires may also be used to rotate the clot extraction catheter to adjust its orientation within a bodily vessel or cavity. The control wires may be attached to the rim directly or one or more of the control wires may be coupled to a nipple or protrusion from the rim. In some embodiments, the control wires may each comprise proximal portions which are fixed to one another.

The control wires may be retracted proximally to capture a clot or thrombus once the self-expanding rim and expandable tubular mesh is advanced and positioned distally of the clot or thrombus. The expandable tubular mesh, once capturing the blood clot, may be closed by advancing the inner sheath over the control wires and at least a portion of the expandable tubular mesh. Alternatively or in combination, the inner sheath may be advanced over the control wires and at least a portion of the expandable tubular mesh. In some embodiments, the two chord control wires are advanced further than the main wire to change the angle of the rim to a more obtuse angle relative to the longitudinal axis of the inner sheath to facilitate advancement of the inner sheath over the control wires. The expandable tubular mesh and the captured clot or thrombus may be gradually molded to the inner diameter of the inner sheath and/or the outer sheath. While very chronic and organized thrombus may resist deformation and molding, such clots may crumble in the expandable tubular mesh when withdrawn into the inner sheath and/or the outer sheath.

In some embodiments, the distal end of the inner and/or outer sheaths may be flared and/or may be configured to flare to accommodate the tubular mesh and the captured clot or thrombus therein. For example, the sheath(s) may comprise partial depth slits parallel to the longitudinal axis of the sheath(s) at the distal end of the sheath(s) or the wall of the sheath(s) may be gradually thinner toward the distal end to allow expansion of the sheath diameter.

The distal end of the expandable tubular mesh may be substantially closed and the proximal end of the expandable tubular mesh may be open. The expandable tubular mesh may be made of mylar, nitinol, or some other resilient and/or expandable material. The length, diameter, and/or pore size of the expandable tubular mesh may vary according to a desired specific task or other factors. Such tasks or factors may include the clot burden to be removed, the diameter of the vessel to be treated, etc.

The expandable tubular mesh may have a pore size. For clot removal, the tubular mesh may have a pore size sufficiently large to allow normal blood cells not to be captured and sufficiently small to allow thrombus to be captured. For distal embolic protection, the pore size may be sufficiently large to allow normal blood cells not to be captured and sufficiently small to allow atheroemboli as small as 20 microns, frequently as small as 10 microns, to be captured.

The inner sheath may be retractably mounted over the expandable tubular mesh to constrain the tubular mesh in the constrained configuration. The inner sheath may be distally advanced to engage the proximal end of the tapered tip to circumscribe and constrain the expandable tubular mesh and may be proximally retracted to release the expandable tubular mesh from constraint so that the mesh self-expands into the expanded configuration.

The clot extraction catheter may further comprise an inner pusher tube advancable within the inner sheath. The inner pusher tube, when advanced, may be disposed within the lumen of the inner sheath and in-between the control wires. The pusher tube may comprise a guidewire lumen through which a guidewire can be passed through. The pusher tube may be used to facilitate advancement of the clot extraction catheter through a subject's vasculature to reach a clot. The pusher tube may facilitate advancement of the clot extraction catheter through tortuous vasculature. For example, the pusher tube may be used to advance the clot extraction catheter through a femoral artery, through the inferior vena cava (IVC), and through the right atrium and ventricle of the heart to reach a pulmonary artery. Alternatively or in combination, the clot extraction catheter may be advanced through this tortuous vasculature without the aid of the inner pusher tube. The clot extraction catheter and its component elements such as the inner sheath may be sufficiently flexible and compliant such that it may navigate through the tortuous vasculature while accommodating for the twists and turns of the vasculature and while minimizing the exertion of any damaging force to the vessel walls.

In some embodiments, the clot extraction catheter comprises a guidewire channel. The guidewire channel may be disposed within the expandable tubular mesh and may extend to the tapered tip. The guidewire channel may have a guidewire lumen configured for a guidewire to be threaded therethrough. The control wires may be disposed radially over the guidewire channel. The inner and/or outer sheaths may be advancable over the guidewire channel. In some embodiments, the control wire sheath may be disposed within the inner sheath. The control wire sheath may house at least a portion of the control wires, typically the proximal portions.

In some embodiments, the clot extraction catheter further comprises at least one clot maceration wire disposed over the guidewire channel. The one clot maceration wire(s) may be manipulated to macerate or break apart a blood clot. The clot maceration wire may have a self-expandable distal portion, which may have a tangled, helical, spiral, linear, or the like configuration. The clot extraction catheter may further comprise a clot maceration wire sheath advancable over the self-expandable distal portion of the maceration wire(s) to collapse the distal portion. The clot maceration wire sheath may be disposed within the inner sheath.

Aspects of the present disclosure may further provide a system for extracting a clot from a blood vessel. The system may comprise the clot extraction catheter as described herein. The system may further comprise a guidewire advancable within the inner sheath of the clot extraction catheter. The guidewire may comprise a bulb near a distal end of the guidewire and may also comprise a soft, floppy tip distal to the bulb. The bulb of the guidewire may be used to facilitate retraction of the tubular mesh and/or inner sheath. The distal end of the tapered tip distal of the tubular mesh may abut the bulb as the guidewire is retracted. Afterwards, further retraction of the guidewire may additionally retract the tubular mesh and/or inner sheath. The guidewire may be used to facilitate the advancement of the clot extraction catheter through a subject's vasculature to reach a clot. The guidewire may first be advanced through the vasculature to reach a target location before the clot extraction catheter is advanced over the guidewire. For example, the guidewire and/or clot extraction catheter may be introduced into the vasculature initially through a jugular or femoral vein before reaching the superior vena cava (SVC) or inferior vena cava (IVC), respectively.

When used as a clot retrieval device, the clot extraction catheter described herein can be used in conjunction with a distal embolic protection device.

Aspects of the disclosure also provide methods for extracting a clot from a bodily vessel or cavity. A distal end of a tapered tip of a clot extraction catheter may be positioned in a lumen of the bodily vessel or cavity proximal of a clot. The tapered tip may be advanced past the clot such that a proximal end of the tapered tip is distal of the clot. A rim coupled to a proximal end of a tubular mesh of the clot extraction catheter may be opened to open the proximal end of the tubular mesh. The tubular mesh may be retracted proximally to capture the clot within the tubular mesh. The rim may be closed to close the proximal end of the tubular mesh and enclose the captured clot within the tubular mesh. The clot extraction catheter may then be removed from the lumen of the bodily vessel or cavity.

An angle of the opened rim relative to a shaft of the clot extraction catheter may also be adjusted before or during retracting of the tubular mesh to capture the clot. This adjustment may be made by proximally or distally translating a main control wire of the clot extraction catheter coupled to the rim independently from proximally or distally translating at least two chord control wires of the clot extraction catheter. Alternatively or in combination, this adjustment may be made by proximally or distally translating a first chord control wire of the at least two chord control wires independently from proximally or distally translating a second chord control wire of the at least two chord control wires.

The rim coupled to the proximal end of the tubular mesh may be opened to allow the rim to self-expand. To allow the rim to self-expand, an inner sheath of the clot extraction catheter may be retracted relative to the rim. Alternatively or in combination, the rim may be advanced out of the inner sheath. To close the rim and enclose the captured clot within the tubular mesh, the tubular mesh may be retracted proximally at least partially into a lumen of the inner sheath. Alternatively or in combination, the inner sheath may be advanced over the tubular mesh enclosing the captured clot. Further, the outer sheath may be used to enclose the tubular mesh with the captured clot (for example, where the inner sheath only partially encloses the tubular mesh with the captured clot). The outer sheath may be advanced over the tubular mesh with the captured clot to fully enclose the tubular mesh before the clot extraction catheter is removed from the bodily vessel or lumen. Alternatively or in combination, the tubular mesh with the captured clot may be retracted proximally into a lumen of the outer sheath.

To position the distal end of the tapered tip of a clot extraction catheter in the lumen of the bodily vessel or cavity proximal of a clot, the clot extraction catheter may be distally advanced with a pusher tube. Alternatively or in combination, a guidewire may be advanced through the bodily vessel or cavity and the clot extraction catheter may be advanced over the guidewire.

In some embodiments, the method may further comprise a step of expanding an expandable element proximal of the opened rim. Proximally retracting the tubular mesh to capture the clot with the tubular mesh may also push the clot against the expanded expandable element. Alternatively or in combination, the expanded expandable element may be advanced toward the opened rim. To advance the expandable element toward the open rim, the inner sheath, a pusher sheath (further described herein), or a control wire sheath (further described herein) on which the expandable element is mounted may be advanced or otherwise translated.

In some embodiments, the method may further comprise a step of expanding at least one clot maceration wire adjacent to the clot. The clot may be macerated with the clot maceration wire prior to retraction of the tubular mesh to capture the macerated clot. The expanded clot maceration wire may then be collapsed by advancing a clot maceration wire sheath over its expanded portion.

The clot extraction catheter described herein may be used to extract a clot, thrombus, or other materials in a bodily vessel or cavity. This bodily vessel or cavity may comprise a blood vessel such as a vein, an artery, the aorta, a pulmonary artery, a vena cava, an inferior vena cava (IVC), a superior vena cava (SVC), an internal jugular vein, an external jugular vein, a subclavian vein, a hepatic vein, a renal vein, an iliac vein, a common iliac vein, an internal iliac vein, an external iliac vein, a femoral vein, or a peripheral vein.

In some embodiments, the clot extraction catheter is positioned proximal of the clot by advancing the clot extraction catheter over a guidewire. The clot extraction catheter may comprise a guidewire channel in which the guidewire is disposed.

In many embodiments, the at least one clot maceration wire comprises a plurality of maceration wires arranged into a macerator. The macerations of the macerator may have any number of configurations such as spiral, helical, curved, straight, zig-zag or any combination thereof. The macerator may be self-expandable or radially expanded by axial contraction. The macerator may be actuated (e.g., rotated and/or translated) to macerate or break apart clot material and thrombus. The macerator may be actuated independently of the chord wire(s) and/or expandable ring.

Aspects of the present disclosure may comprise clot extraction catheters. An exemplary clot extraction catheter may comprise an expandable tubular mesh, a self-expanding rim, at least one control wire, an inner sheath, and at least one clot maceration wire. The expandable tubular mesh may have a distal end and a proximal end. The tubular mesh may have an expanded configuration and a constrained configuration. The self-expanding rim may be attached to the proximal end of the expandable tubular mesh. The self-expanding rim may have an unconstrained diameter which is greater than a width of the proximal end of the tapered tip. The at least one control wire may be attached to the self-expanding rim and disposed radially over the guidewire channel. The inner sheath may be advancable over the at least one control wire to constrain at least a portion of the self-expanding rim and at least a portion of the tubular mesh within a lumen of the inner sheath. The at least one clot maceration wire may be advancable from the inner sheath and may be radially expandable to facilitate clot maceration. The at least one control wire may be configured to be manipulated to control an angle of the self-expanding rim relative to an axis of the inner sheath when the self-expanding rim is unconstrained.

The clot extraction catheter may further comprise an outer sheath advancable over the inner sheath and the guidewire channel. The clot extraction catheter may further comprise an expandable element, and the expandable element may be mounted on a distal end of the outer sheath or on a pusher sheath that may be translatable relative to one or more of the inner or outer sheaths.

The clot extraction catheter may further comprise a tapered tip fixed to the end of the expandable tubular mesh. The clot extraction catheter may further comprise a guidewire channel disposed within the expandable tubular mesh and extending to the tapered tip. The guidewire channel may have a guidewire lumen configured for a guidewire to be threaded therethrough. The clot extraction catheter may further comprise one or more other features as described herein.

The at least one control wire may comprise a plurality of control wires. The plurality of control wires may comprises at least three control wires which may comprises a main wire and two chord wires. The main wire may be translatable proximally and distally. The two chord wires may be translatable proximally and distally independently from the main wire to control the angle of the self-expanding rim relative to the axis of the shaft when the self-expanding rim is unconstrained.

The at least one clot maceration wire may comprise a plurality of clot maceration wires. The at least one clot maceration wire may have one or more of a helical, spiral, sinusoidal, zig-zag, bracketed, curved, linear, tangled, or curvilinear shape. The at least one clot maceration wire may comprise any of the clot macerators or clot maceration elements described herein.

The proximal end of the expandable tubular mesh may be open. The self-expanding ring and the at least one clot maceration wire may be axially translatable independently from one another.

Aspects of the present disclosure further provide methods for extracting a clot from a bodily vessel or cavity. The clot extraction catheter may be advanced over a guidewire to position a distal end of a tapered tip of the clot extraction catheter in a lumen of the bodily vessel or cavity proximal of a clot. The guidewire may be disposed within a guidewire channel of the clot extraction catheter. The tapered tip may be advanced past the clot such that a proximal end of the tapered tip is distal of the clot. A rim coupled to a proximal end of a tubular mesh of the clot extraction catheter may be opened to open the proximal end of the tubular mesh. The tubular mesh may be retracted proximally to capture the clot within the tubular mesh. The clot may be contacted with at least one clot maceration wire of the clot extraction catheter as the tubular mesh is retracted. The rim may be closed to close the proximal end of the tubular mesh and enclose the captured clot within the tubular mesh. The clot extraction catheter may be removed from the lumen of the bodily vessel or cavity.

The step of contacting the clot with the at least one clot maceration wire may comprise macerating the clot with the at least one maceration wire. Macerating the clot may comprise one or more of axially translating or rotating the at least one clot maceration wire contacting the clot. The at least one clot maceration wire may comprises a plurality of maceration wires. The at least one clot maceration wire may comprise any of the clot macerators or clot maceration elements described herein.

In some embodiments, the at least one clot maceration wire may be radially expanded. In some embodiments, an angle of the opened rim may be adjusted before or during retracting of the tubular mesh to capture the clot.

The blood vessel from which the clot may be extracted and/or macerated may be any blood vessel, for example, such as one selected from the group comprising a vein, an artery, the aorta, a pulmonary artery, a vena cava, an inferior vena cava (IVC), a superior vena cava (SVC), an internal jugular vein, an external jugular vein, a subclavian vein, a hepatic vein, a renal vein, an iliac vein, a common iliac vein, an internal iliac vein, an external iliac vein, a femoral vein, and a peripheral vein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows a side view of a clot extraction catheter having its tubular mesh clot capture basket constrained, in accordance with many embodiments;

FIG. 1B shows a side sectional view of the clot extraction catheter of FIG. 1A having its tubular mesh clot capture basket constrained;

FIG. 1C shows a side view of the clot extraction catheter of FIG. 1A having its tubular mesh clot capture basket unconstrained;

FIG. 1D shows a side sectional view of the clot extraction catheter of FIG. 1A having its tubular mesh clot capture basket unconstrained;

FIGS. 2A to 2K show sectional views of the clot extraction catheter of FIG. 1A in use to remove a clot or thrombus in a blood vessel;

FIG. 5A shows a side view of a clot extraction catheter having its tubular mesh clot capture basket constrained, in accordance with many embodiments;

FIG. 5B shows a side sectional view of the clot extraction catheter of FIG. 5A having its tubular mesh clot capture basket constrained;

FIG. 5C shows a side view of the clot extraction catheter of FIG. 5A having its clot capture basket unconstrained;

FIG. 5D shows a side sectional view of the clot extraction catheter of FIG. 5A having its tubular mesh clot capture basket unconstrained;

FIG. 5E shows a cross-sectional view of the clot extraction catheter of FIG. 5A taken through line 5E in FIG. 5D;

FIG. 5F shows a schematic of the middle working portion of the clot extraction catheter of FIG. 5A;

FIG. 6A shows a side view of the distal or working end of a clot extraction catheter, in accordance with many embodiments;

FIG. 6B shows a side view of the proximal or handle end of the clot extraction catheter of FIG. 6A;

FIG. 7A shows a side view of a clot extraction catheter with an expandable element, according to many embodiments;

FIG. 7B shows a cross-sectional view of the clot extraction catheter of FIG. 7A;

FIGS. 10A, 10B, 10C, and 10D show sectional side views of a clot extraction catheter having a plurality of clot maceration elements, according to many embodiments;

FIG. 13B shows a side view of the macerator structure for a clot extraction catheter of FIG. 13A;

FIG. 13C shows an end view of a macerator structure for a clot extraction catheter having a combination of linear macerator elements, according to many embodiments;

FIG. 14A shows a perspective view of a macerator structure for a clot extraction catheter having a combination of spiral or helical macerator elements, according to many embodiments;

FIG. 14B shows a side view of the macerator structure for a clot extraction catheter of FIG. 14A.

FIG. 14C shows an end view of the macerator structure for a clot extraction catheter of FIG. 14A.

FIG. 15A shows a side view of a macerator structure for a clot extraction catheter having spiral or helical elements, according to many embodiments;

FIG. 15B shows an end view of the macerator structure for a clot extraction catheter of FIG. 15A.

FIG. 18A shows the net extended and axially collapsed and macerator collapsed; FIG. 18B shows the net extended and axially collapsed and the macerator expanded; and, FIG. 18C shows the net retracted and axially extended and the macerator expanded;

FIG. 19A shows the net extended and axially collapsed and macerator expanded with attached guide wires; and, FIG. 19B shows the net retracted and axially extended over the expanded macerator elements by the plurality of guide wires;

FIGS. 20A and 20B show side views of an exemplary clot extraction catheter having spiral or helical macerator elements being used to capture and macerate a clot, according to many embodiments;

FIGS. 21A, 21B, and 21C show side views of an exemplary clot extraction catheter having its macerator expanded and then twisted, according to many embodiments; FIG. 21A shows the macerator collapsed; FIG. 21B shows the macerator expanded; and, FIG. 21C shows the macerator expanded and twisted;

FIGS. 22A and 22B show cross-sectional side views of a clot extraction catheter used for thrombolysis and aspiration, according to many embodiments;

DETAILED DESCRIPTION

Figure 2A:
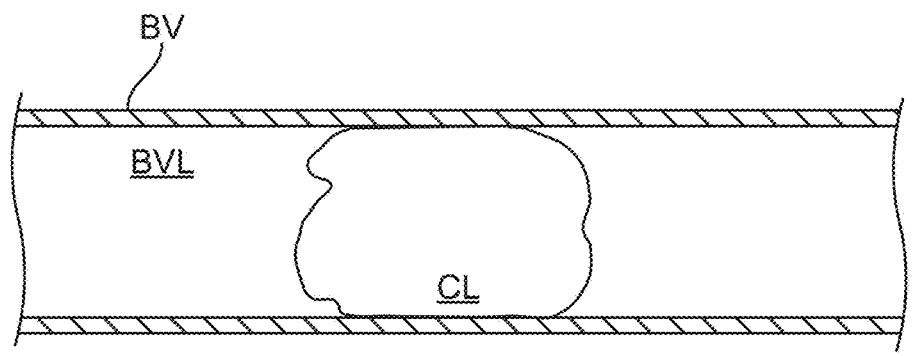

FIGS. 1A to 1D show a clot extraction catheter 100 according to many embodiments. FIGS. 1A and 1B show the clot extraction catheter 100 with its tubular mesh or clot capture basket 110 in a constrained, delivery configuration. The tubular mesh or clot capture basket 110 may be self-expanding and may comprise a shape-memory material or metal such as Nitinol (NiTi). The clot extraction catheter 100 comprises a tubular inner sheath 140 which is advancable over the tubular mesh 110 to constrain the tubular mesh 110. The tubular inner sheath 140 can be retracted proximally to release the tubular mesh 110 as shown in FIGS. 1C and 1D. When unconstrained, the tubular mesh 110 may resiliently assume its unconstrained configuration which may be in the form of a tube sock-like structure. Alternatively or in combination, the tubular mesh 110 may comprise a heat-based shape memory material so that the unconstrained tubular mesh 110 may assume the tube sock-like structure when exposed to body temperatures in a bodily vessel or cavity. The clot extraction catheter 100 may further comprise an outer sheath 170 which may be advanced over the tubular inner sheath 140 (or the tubular inner sheath 140 may be retracted to be within the outer sheath 170). The outer sheath 170 may have a width or diameter of 8-25 Fr, for example. The inner sheath 140 and/or outer sheath 170 may comprise proximal side arms (e.g., for the passage of a guidewire, fluid infusion, etc.) and/or injection ports. The inner sheath 140 and/or outer sheath 170 may also be provided with one or more radiopaque markers to facilitate locating the inner sheath 140 and/or outer sheath 170 as they are advanced through the vasculature.

The clot extraction catheter 100 may further comprise an atraumatic, dilator tip 120. The dilator tip 120 may be elongate in shape and tapered with a straight surface to facilitate the passage of the tip 120 through a clot without pushing the clot. The dilator tip has a distal end 122 and a proximal end 124. The proximal end 124 may be rounded so that the dilator tip 120 is atraumatic when proximally retracted. The width or diameter of the dilator tip 120 at the proximal end 124 may be slightly greater than the width or diameter of the tubular inner sheath 140. The distal end 142 of the tubular inner sheath 140 may abut the proximal end 124 of the dilator tip 120 when distally advanced. The proximal end 124 of the dilator tip 120 may be attached or fixed to a distal portion 112 of the tubular mesh 110. The outer sheath 170 may have a width or diameter such that it may be advanced over the dilator tip 120. In some embodiments, the outermost diameter of the dilator tip 120 may match the innermost diameter of the distal end of the outer sheath 170 such that the dilator tip 120 may be fitted to the distal end of the outer sheath 170 when retracted. Alternatively or in combination, the distal end of the outer sheath 170 may be flared.

The distal portion 112 of the tubular mesh 110 may be tapered. This tapering may end at the distal end 116 of the tubular mesh 110. The distal end 116 of the tubular mesh 110 may be coupled to the dilator tip 120. The distal end 122 of the dilator tip 120 may be coupled to the distal end 116 of the tubular mesh 110 as well. A guidewire 160 may be passed through the lumen of the inner sheath 140 and disposed in-between the control wires 132, 134a, 134b. The guidewire 160 may have a diameter of 0.025 inches, for example. The guidewire 160 may comprise a bullet or bulb 162 near the distal end of the guidewire 160. The bullet or bulb 162 may have a width or diameter greater than that of the distal end 122 of the dilator tip 120 such that distal advancement of the clot extraction catheter 100 may be limited. The clot extraction catheter 100 may be distally advanced until the distal end 122 of the dilator tip 120 abuts the bullet or bulb 162. The bullet or bulb 162 may have a diameter of 0.035 inches, for example. The bullet or bulb 162 may also facilitate in the navigation of the guidewire 160 through tortuous vasculature as well facilitate advancement of the guidewire 160 through clot, thrombus, emboli, or the like in a bodily vessel or lumen.

The open proximal end 114 of the tubular mesh 110 may be coupled to a rim or ring 130. The rim or ring 130 may be self-expanding. When unconstrained by the inner sheath 140, the rim or ring 130 may resiliently expand to facilitate the opening and expansion of the tubular mesh 110. The rim or ring 130 may comprise a shape-memory material such as Nitinol (NiTi) to facilitate self-expansion. The shape-memory material may be heat-based, for example, so that the rim or ring 130 may assume its expanded configuration when exposed to bodily temperatures in a bodily vessel or cavity.

At least three control wires 132, 134a, 134b may be coupled to the rim or ring 130. The control wires may comprise a main control wire 132 and two chord wires 134a, 134b. The control wires 132, 134a, 134b may be disposed within the inner sheath 140 and run the length of the clot extraction catheter 100 proximally from the rim or ring 130. The control wires 132, 134a, 134b may be independently manipulated at a proximal, handle end of the clot extraction catheter 100. The main control wire 132 may be translated either distally or proximally independently from the distal or proximal translation of the two chord wires 134a, 134b. In some embodiments, each of the chord wires 134a, 134b may be independently translated from each other as well. The control wires 132, 134a, 134b may be manipulated to change the angle of the expanded rim 130 relative to the longitudinal axis of the inner sheath 140. The attachment points of the control wires 132, 134a, 134b may be evenly distributed over the circumference of the rim 130. The control wires 132, 134a, 134b may have a width of 0.010 inches, for example. In some embodiments, the chord wires 134a, 134b may be thinner than the main wire 132. In alternative embodiments, two or more of the control wires 132, 134a, 134b may be attached to one another at proximal portions thereof such that they may be user manipulated in conjunction. Also, while three control wires are shown in FIGS. 1A to 1D, alternative number of control wires (such as one, two, or four or more) may be provided instead.

FIGS. 2A to 2K show the clot extraction catheter 100 in use to capture a clot CL in the lumen BVL of a blood vessel BV. The blood vessel BV may be selected from the group comprising a vein, an artery, a pulmonary artery, a vena cava, an inferior vena cava (IVC), a superior vena cava (SVC), an internal jugular vein, an external jugular vein, a subclavian vein, a hepatic vein, a renal vein, an iliac vein, a common iliac vein, an internal iliac vein, an external iliac vein, a femoral vein, a peripheral vein, and a peripheral artery, for example. The clot extraction catheter 100 may also be used to capture other solid, biological material in other bodily vessels or cavities such as the ureter, urethra, renal pelvis, bladder, intestines, esophagus, stomach, small intestines, large intestines, colon, vagina, uterus, trachea, and bronchus, to name a few.

Figure 2B:
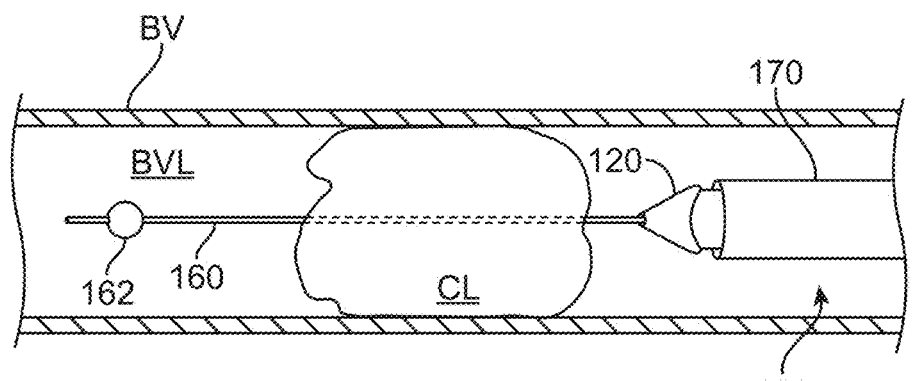

As shown in FIG. 2A, a blood vessel lumen BVL may have a clot CL lodged therein. In some embodiments, a diagnostic catheter and guidewire may be passed through the clot CL, followed by an exchange of the diagnostic catheter with the guidewire 160 as shown in FIG. 2B. In some embodiments, an angioplasty catheter may be advanced through clot CL either through the diagnostic catheter or the guidewire 160 and the clot CL may be expanded to facilitate the later advancement of the clot extraction catheter 100 therethrough.

As shown in FIG. 2B, the guidewire 160 and bulb 162 may be advanced through the clot CL. The clot extraction catheter 100 may be advanced over the guidewire 160 to be positioned just proximally of the clot CL. At this point, most of the elements of the clot extraction catheter 100 remain housed within the outer sheath 170. The tapered, dilator tip 120 may be exposed.

Figure 2C:
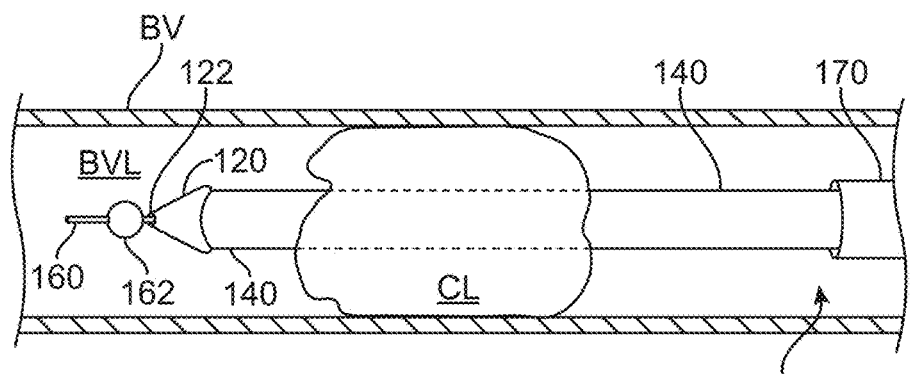

As shown in FIG. 2C, the clot extraction catheter 100 may be advanced through the clot CL. In particular, the inner sheath 140 and the dilator tip 120 may be advanced from the outer sheath 170 through the clot CL. The inner sheath 140 and the dilator tip 120 may be advanced through the clot CL until the distal end 122 of the dilator tip 120 abuts the bulb 162 of the guidewire 160.

As shown in FIG. 2D, the inner sheath 140 may now be retracted proximally and/or the tubular mesh 100 and the self-expanding rim or ring 130 advanced distally so that the tubular mesh 110 and the self-expanding rim or ring 130 are unconstrained and expanded just distal of the clot CL. The tubular mesh 110 of the clot extraction catheter may be telescoped up to itself to shorten the mesh 100 beyond the clot, e.g., by advancing the tapered tip 120 to the bulb 162 and pushing the rim 130 forward toward the bulb 162. The guidewire 160 with the bulb 162 may also be pulled proximally to pull the dilator tip 120 proximally to facilitate the telescoping and shortening of the tubular mesh 110.

As shown in FIG. 2E, the inner sheath 140 may instead be retracted proximally and/or the tubular mesh 110 and the self-expanding rim or ring 130 advanced distally so that the tubular mesh 110 and the self-expanding rim or ring 130 are unconstrained and expanded with little or no telescoping. The expanded tubular mesh 110 and rim/ring 130 may be positioned immediately distal of the clot CL.

Figure 2F:
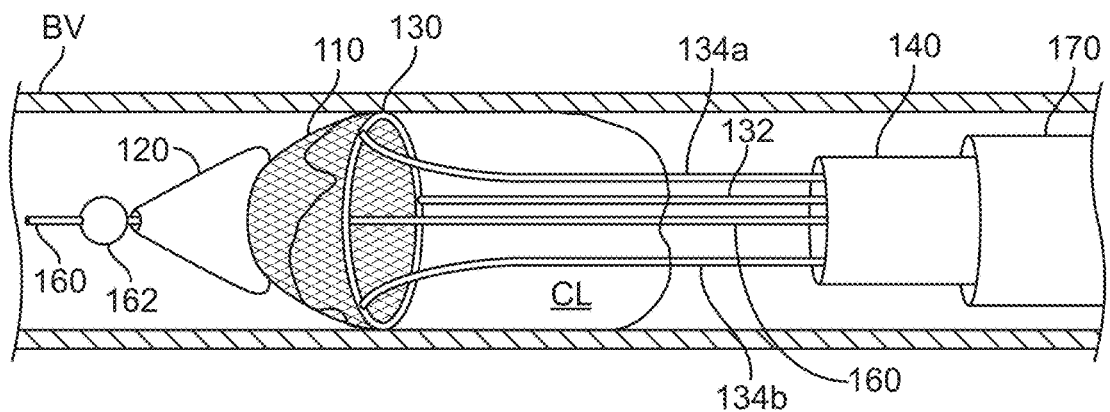
Figure 2G:
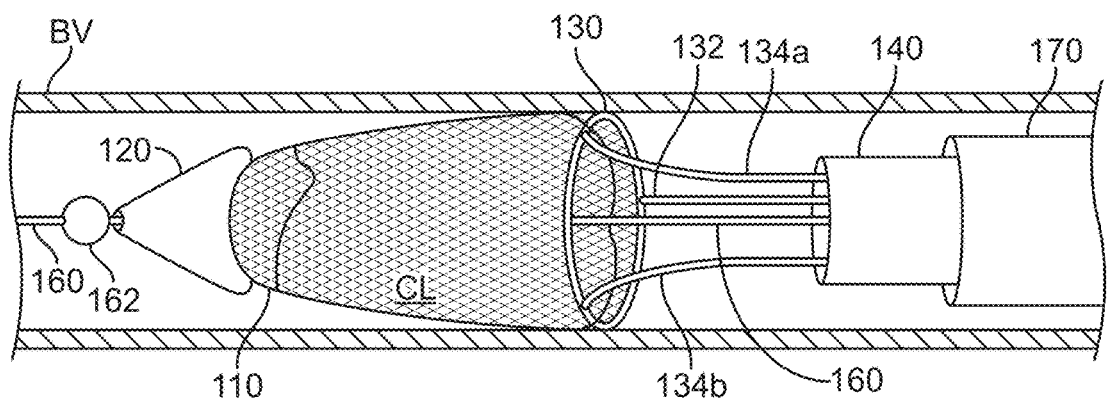

As shown in FIGS. 2F and 2G, the expanded tubular mesh 110 may be proximally retracted partially as shown in FIG. 2F and then completely as shown in FIG. 2G to capture the clot CL within the tubular mesh 110. The tubular mesh 110 may proximally retracted by proximally retracting one or more of the main control wire 132, or the two chord wires 134a, 134b. As the expanded tubular mesh 110 is retracted, the tubular mesh 110 may expand at least axially to accommodate any captured clot CL.

Figure 2H:
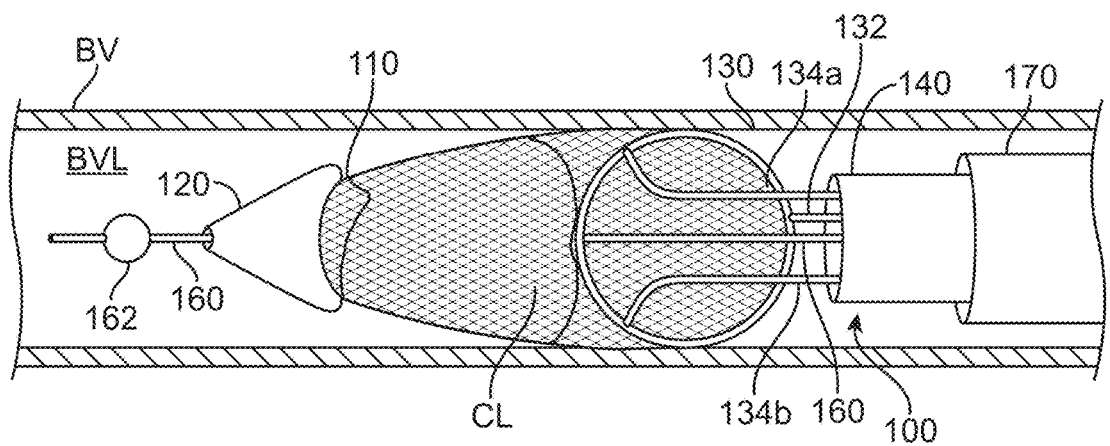
Figure 2I:
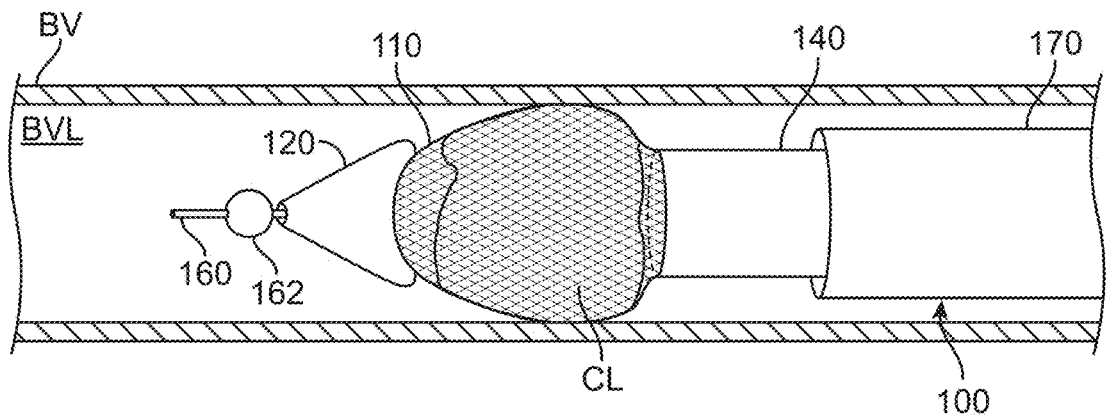

As shown in FIGS. 2H and 2I, the angle of the rim 130 relative to the longitudinal axes of the inner sheath 140 and/or outer sheath 170 may be controlled to facilitate capture of the clot CL or the retraction of the tubular mesh 110 and the rim 130 first constrained by the distal portion of the inner sheath 140 and back within the outer sheath 170. The rim 130 angle may be initially be 0° as shown in FIGS. 2E to 2G but may be manipulated to be 45° as shown in FIG. 2H. This angle may be controlled by manipulating one or more of the control wires 132, 134a, or 134b. As shown in FIG. 2H, the two chord control wires 134a, 134b may be advanced distally and/or the main control wire 132 may be retracted proximally to control the angle. By providing three or more control wires, the rim 130 angle may be controlled with two or more degrees of freedom. Alternatively or in combination, the clot extraction catheter 100 may be rotated to control the orientation of the rim 130 and the tubular mesh 110. In other embodiments, the control wires 132, 134a, 134b may have a fixed orientation relative to one another such that the rim 130 angle may be fixed (such as to 45°, for example.)

As shown in FIG. 2I, the rim and the tubular mesh 110, including the clot CL captured therein, may be proximally retracted partially into the inner sheath 140 (i.e., the proximal portion of the tubular mesh 110 may be retracted into and constrained by the inner sheath 140). This may partially or completely close the rim 130 and the mesh 110. In some embodiments, the distal end of the inner sheath 140 may be flared and/or may become flared as the tubular mesh 110 and the captured clot CL are retracted to facilitate such retraction.

Figure 2J:
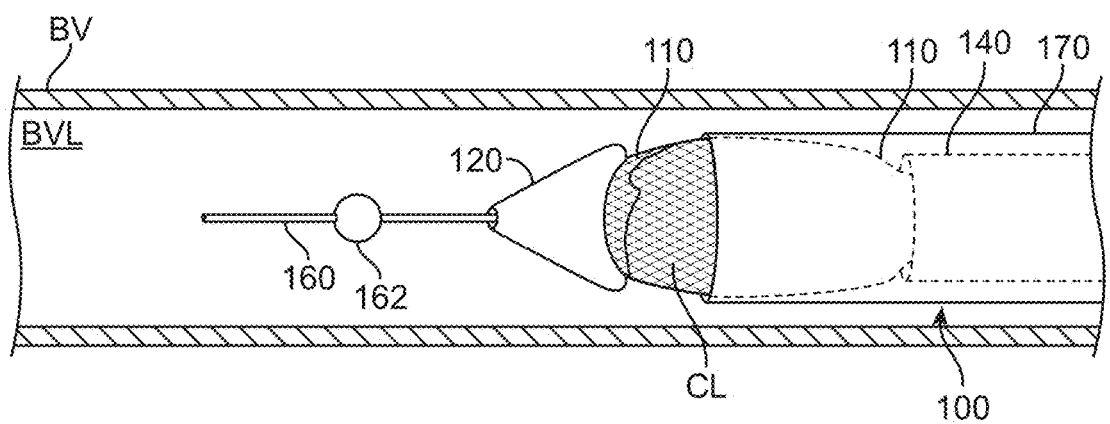

As shown in FIG. 2J, as the captured clot CL is retracted into the outer sheath 170, the outer sheath 170 may change the shape of the clot CL and may break apart or cause the crumbling of the larger particles of the clot CL. The captured clot CL, the tubular mesh 110, and the inner sheath 140 may be fully retracted into the outer sheath such that the clot extraction catheter assumes the configuration shown by FIG. 2B.

Figure 2K:
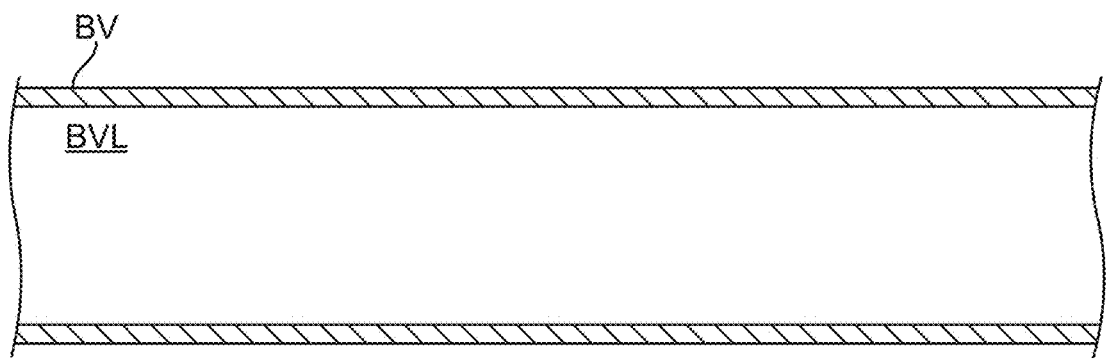

As shown in FIG. 2K, the clot extraction catheter 100 and the guidewire 160 may then be removed from the blood vessel BV to leave the blood vessel lumen BVL free and clear of any clot. In some cases, the clot extraction catheter 100 is retracted before the guidewire 160 is retracted. The guidewire 160 can be left in place to facilitate blood vessel access and optionally further treatment or intervention. If further clot extraction may be necessary, the guidewire 160 and the outer sheath 170 may both be left in place and only the inner sheath 140 and clot extraction catheter 100 with the captured clot CL removed. The amount of clot removed can be ascertained by introducing a diagnostic catheter over the guidewire 160 and contrast angiography performed over the wire. The clot extraction catheter and the inner sheath 140 may be cleaned and reinserted into the outer sheath 170, or a new different sized clot extractor 100 and its inner sheath 140 may be introduced.

Figure 3:
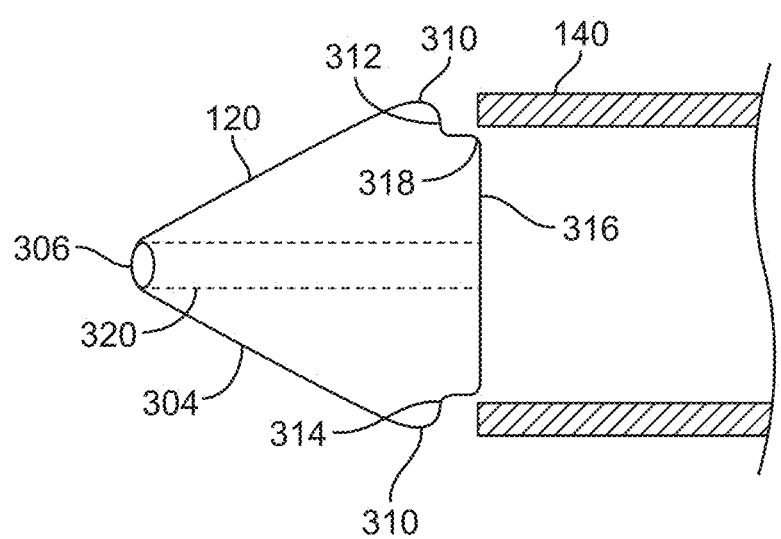
FIG. 3 illustrates a partial cross-section of the dilator tip.

FIG. 3 illustrates an exemplary embodiment of the dilator tip 120 positioned adjacent the inner sheath 140. The dilator tip 120 and the inner sheath 120 may be any of the embodiments disclosed in this specification. The dilator tip 120 includes a conical tapered outer surface 304, a distal guidewire port 306, guidewire lumen 320 and a proximal end that cooperates with the distal end of the inner sheath 140. The proximal end of the dilator tip 120 includes smooth radius outer edge 310 to minimize vascular trauma during retraction of the dilator tip 120. Flat shoulder 312 can provide a stop against which the distal end of inner sheath 140 may rest. Also, a flat proximal end 316 can facilitate self-centering of the inner sheath 140 when engaged with the proximal end of the dilator tip 120. Inner edges 314, 318 may also have radii in order to prevent vascular trauma and provide a smooth, self-centering transition so that inner sheath 140 is easily advanced and aligned with the proximal end of the dilator tip 120.

Figure 4:
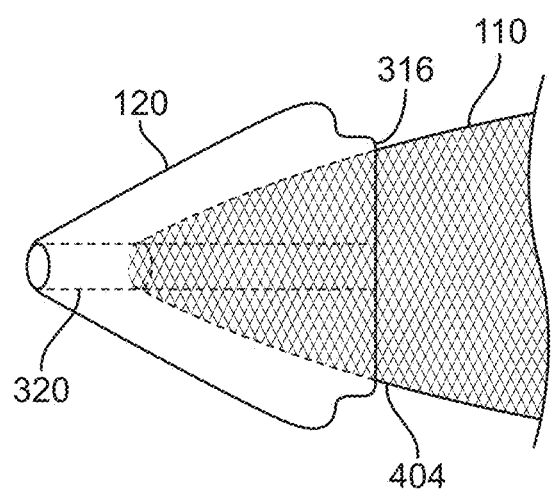
FIG. 4 illustrates the tubular mesh coupled to the dilator tip.

FIG. 4 illustrates the tubular mesh 110 disposed in the dilator tip 120. The tubular mesh and the dilator tip may be any of the embodiments disclosed herein. The tubular mesh 110 preferably has a width 404 adjacent the proximal end of dilator tip 120 that is less than the width of the flat proximal end 316. This can minimize the possibility of the tubular mesh 110 being trapped or caught by the distal end of inner sheath 140 (not illustrated).

As shown in FIGS. 5A-5E, the clot extraction catheter 100 may further comprise a guidewire channel 150. FIG. 5A shows a side view of the clot extraction catheter 100. FIG. 5B shows a side sectional view of the clot extraction catheter 100 having its tubular mesh clot capture basket 110 constrained. FIG. 5C shows a side view of the clot extraction catheter 100 having its clot capture basket 110 unconstrained. FIG. 5D shows a side sectional view of the clot extraction catheter 100 having its tubular mesh clot capture basket 110 unconstrained. FIG. 5E shows a cross-sectional view of the clot extraction catheter of FIG. 5A taken through line 5E in FIG. 5D. FIG. 5F shows a schematic of the middle working portion of the clot extraction catheter 100, including the rim or ring 130 of the tubular mesh clot capture basket 110 and the control wires 132, 134a, and 134b attached thereto.

As shown in FIGS. 5B-5F, the guidewire channel 150 may be disposed within the lumens of both the inner sheath 140 and the outer sheath 170. The control wires 132, 134a, and 134b may also be disposed circumferentially over the guidewire channel 150. The guidewire channel 150 may extend from the proximal end or portion of the clot extraction catheter 100 to the distal end 122 of the dilator tip 120.

As shown in FIGS. 5E and 5F, the control wires 132, 134a, and 134b may be housed within a control wire sheath 135 that may be retracted within the inner sheath 140. The proximal portions of the chord control wires 134a and 134b may be coupled together to a single control wire 134c which may be actuated in combination with the main control wire 132 to change the pitch or angle of the rim or ring 130 relative to the longitudinal axis of the clot extraction catheter 100. The longitudinal axis of the clot extraction catheter 100 may, for example, be coaxial with one or more of the guidewire 160, the control wire sheath 135, the inner sheath 140, or the outer sheath 170.

Figure 6C:
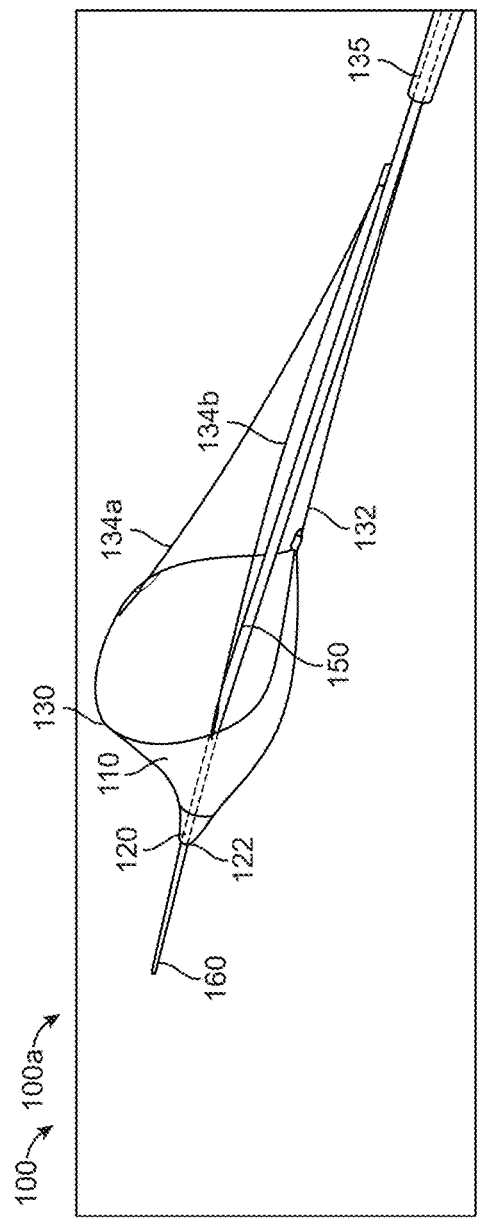
FIG. 6C shows a perspective view of the distal or working end of the clot extraction catheter of FIG. 6A.

FIG. 6A shows a side view of the distal or working end 100a of the clot extraction catheter 100. The distal or working end 100a of the clot extraction catheter 100 may include the dilator tip 120, the tubular mesh clot capture basket 110, the rim or ring 130, the guidewire channel 150, the control wire sheath 135, and the control wires 132, 134a, and 134b. The distal or working end 100a may be retracted within the inner sheath 140. As shown in FIG. 6A, the distal or working end 100a is extended from the inner sheath 140 such that the clot capture basket 110 is in its expanded, unconstrained configuration. The distal or working end 100a may be extended out a distance of 150 mm from the distal end 122 of the dilator tip 120 and the distal end of the inner sheath 140, for example. As discussed above, one or more radiopaque markers may be provided such as on the inner sheath 140 and/or the dilator tip 120 to help the user determine the relative positioning of the different components of the clot extraction catheter 100. FIG. 6C shows a perspective view of the distal or working end 100a of the clot extraction catheter 100.

Figure 6D:
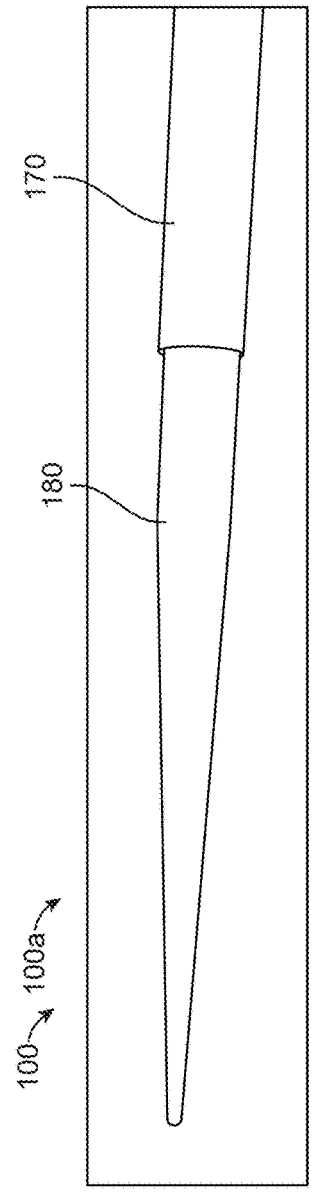
FIG. 6D shows the outer sheath and dilator tip of the clot extraction catheter of FIG. 6A.

FIG. 6B shows a side view of the proximal or handle end 100b of the clot extraction catheter 100. At the proximal or handle end 100b, the proximal end of the inner sheath 140 may be coupled to a hub 172. The hub 172 may be coupled to a suction channel 174 which may provide suction to the lumen of the inner sheath 140. The suction provided by the suction channel 174 may facilitate the removal and retraction of clot captured by the basket 110 when retracted back into the inner sheath 140. The control wire sheath 135 may lead from the hub 172 to a handle 101. The handle 101 may comprise a button or control 101b, such a slider, which may be actuated by the user to control the control wires 132, 134a, and 134b housed within the control wire sheath 135 to adjust the pitch or angle of the rim or ring 130. The handle 101 may comprise an inner lumen such that the guidewire 160 may be threaded through one or more (typically each of) the handle 101, the control wire sheath 135, the hub 172, and the inner sheath 140, for example, through a guidewire channel 150. As discussed above and shown in FIG. 6D, an introduction dilator tip 180 may be threaded through an outer sheath 170 to facilitate advancement and positioning of the outer sheath 170 and subsequently the clot extraction catheter 100 through tortuous vasculature to be adjacent a clot to be captured.

In some embodiments, an expandable element 191 may be provided to facilitate clot capture in conjunction with the self-expanding rim. The expandable element 191 may typically comprise an inflatable balloon inflatable through an inflation lumen. As the expanded rim or ring 130 is retracted, the clot CL may be pushed against the expanded expandable element 191 to help urge the clot CL into the tubular mesh and prevent clot material from diverting into undesired locations. Alternatively or in combination, the expanded expandable element may 191 be translated to fulfill at least this function.

FIG. 7A shows a side view of a clot extraction catheter 100 with an expandable element 191. The expandable element 191 may be mounted on the distal end of a pusher or balloon sheath or shaft 195. As shown in FIG. 7B, the pusher sheath 195 may be disposed radially in-between the inner, control wire sheath 135 and the inner sheath 140. The pusher sheath 195 may include an inflation lumen to inflate or deflate the expandable element 191.

Figure 8A:
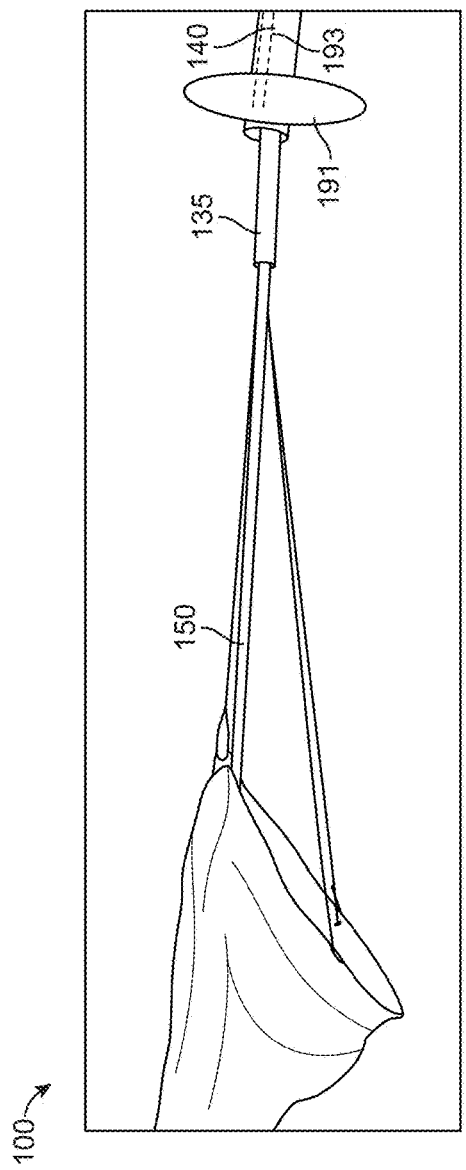
FIG. 8A shows a side view of another the clot extraction catheter with an expandable element, according to many embodiments.
Figure 8B:
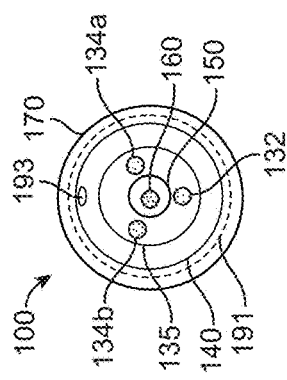
FIG. 8B shows a cross-sectional view of the clot extraction catheter of FIG. 8A.

FIGS. 8A and 8B show side and sectional views, respectively, of another clot extraction catheter 100 having an expandable element 191. The expandable element 191 may be mounted on the distal portion of the inner sheath 140, which may also provide an inflation lumen 193 for the expandable element 191.

FIGS. 9A, 9B, 9C, and 9D show side views of another clot extraction catheter 100 having an expandable element 191. The expandable element 191 may be mounted within the inner sheath 140 and on the control wire sheath 150. The control wires 134a, 134b, and 132 may surround the expandable element 191.

Figure 9A:
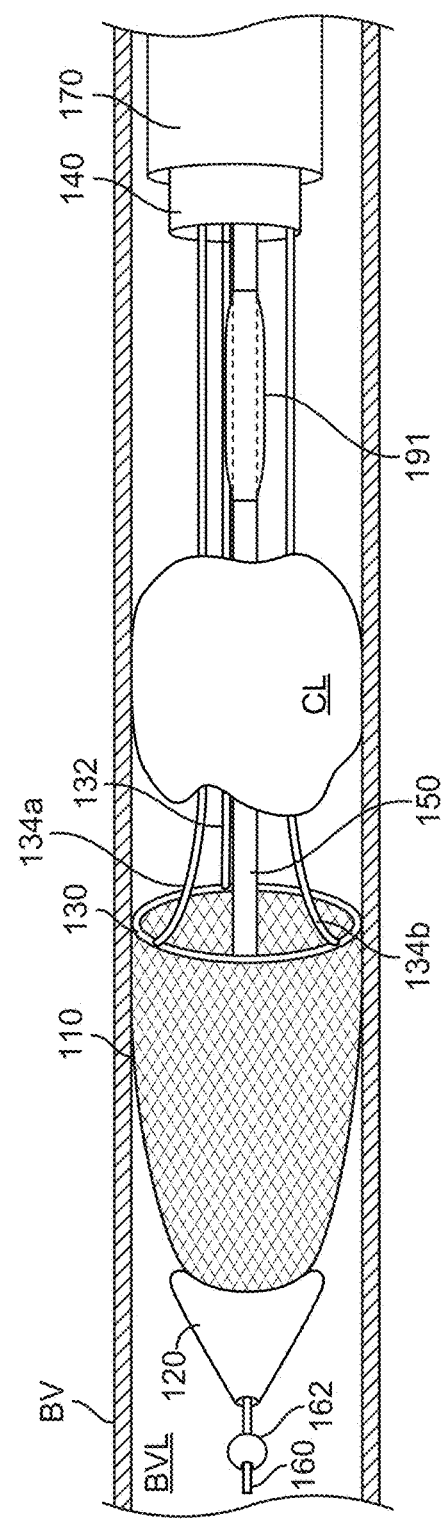
FIGS. 9A, 9B, 9C, and 9D show a method of use for the clot extraction catheter with an expandable element, according to many embodiments.

FIG. 9A shows the expandable ring 130 expanded distally of the clot CL. The expanded expandable element 191 mounted on the control wire sheath 150 is positioned proximally of the clot CL.

Figure 9B:
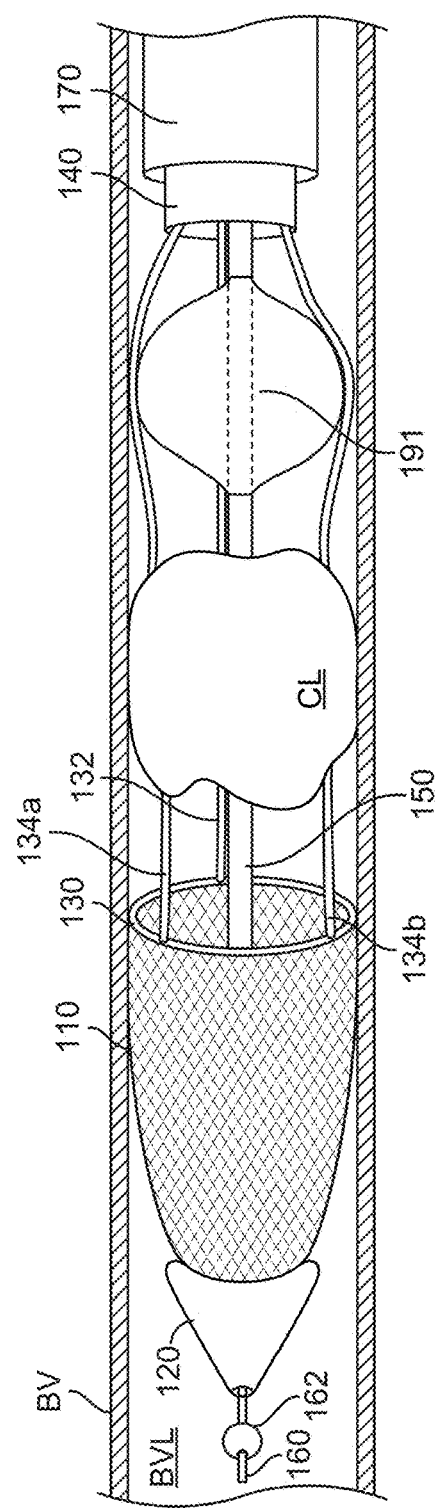

FIG. 9B shows the expandable element 191 being expanded. When expanded, the expandable element 191 may urge the control wires 132, 134a, and 134b laterally outward. To minimize the pushing of the control wires 132, 134a, and 134b against the blood vessel inner wall and possibly causing tissue damage, the maximum size, shape, and/or other parameters of the expandable element 191 may be limited.

Figure 9C:
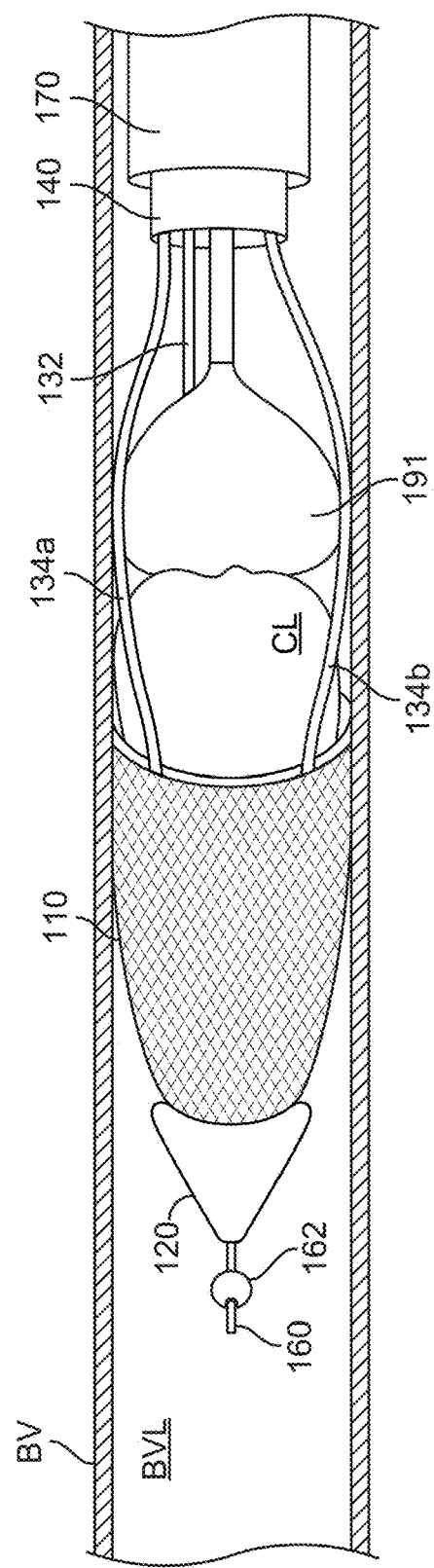
Figure 9D:
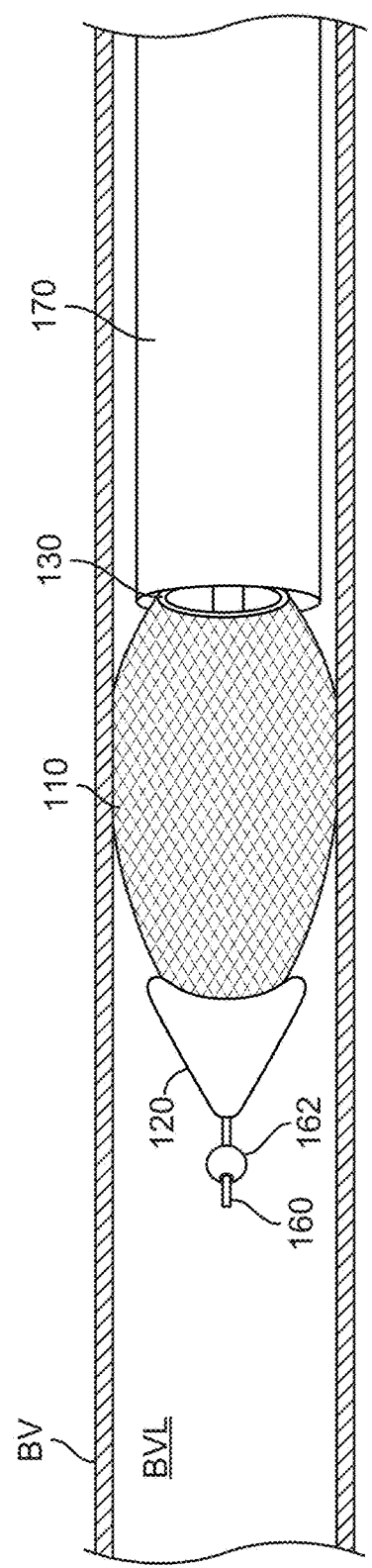

FIG. 9C shows the expanded ring 130 and the expanded expandable element 191 may be urged toward one another to urge the clot CL into the tubular mesh 110. Once the clot CL is fully captured, the expandable element 191 may be collapsed and the tubular mesh 110, including the captured clot CL, may be retracted into the inner sheath 140 and/or the outer sheath 170.

In some embodiments, expandable wire(s) may be provided to facilitate clot capture in conjunction with the self-expanding rim. These expandable wire(s) may be actuated to macerate or break apart clot to facilitate their capture in the tubular mesh 110 or the inner lumen of the inner sheath 140. The use of such expandable wire(s) may be combined with the use of the expandable element described above to facilitate clot capture.

FIGS. 10A-10D show a clot extraction catheter 100 having a plurality of maceration wires 197. The plurality of wires 197 may be coaxial with the guidewire channel 150 and may be disposed over the guidewire channel 150. When the clot extraction catheter 100 is positioned at a target site, the tubular mesh 110 and the self-expanding rim 130 may be advanced distally of the plurality of wires 197 and the clot CL.

The plurality of wires 197 may be collapsed and housed within a maceration wire sheath 197 as shown in FIGS. 10A and 10C. The maceration sheath 199 may be housed within the inner sheath 140. The plurality of maceration wires 197 may have a self-expandable, distal portion. As shown in FIGS. 10A and 10B, the wires 197 may be tangled (randomly, for example) at its distal portion. As shown in FIGS. 10C and 10D, the wires 197 may be helically wound at its distal portion. The wires 197 may be made of a shape memory material and/or metal such as Nitinol so as to be biased to expand to assume the tangled (FIG. 10B) or spiral or helical (FIG. 10D) configurations. The maceration sheath 199 may be retracted to expose the distal portion as shown in FIGS. 10B and 10D. Typically, the distal portion is expanded at the site of the clot CL. Once expanded, the wires 197 may be rotated and/or translated to macerate or break apart the clot CL. The wires 197 can then be collapsed by advancing the maceration sheath 199 thereover. Subsequently, the broken apart clot may be captured by the tubular mesh 110 and the lumen of the inner sheath 140 as described above.

Figure 11:
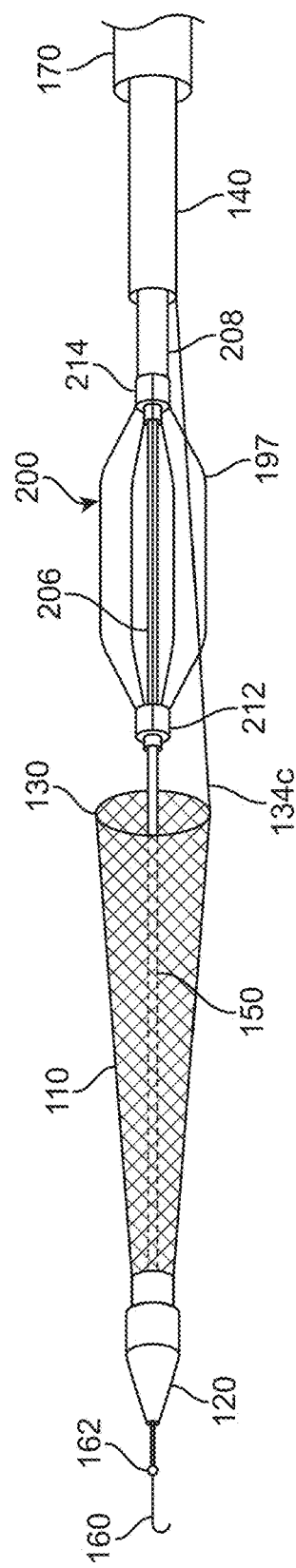
FIG. 11 shows a perspective view of a clot extraction catheter having a plurality of clot maceration elements arranged in a linear configuration, according to many embodiments.

FIG. 11 shows a side view of an exemplary clot extraction catheter 100 in its extended configuration with a capture basket 110 deployed. As shown, the macerator 200 may comprise a plurality of maceration wires 197 having a linear configuration. Alternatively or in combination, the maceration wires 197 may be partially or fully straight, round, bent, helical about an axis, or have a profile that is random, or any combination thereof. The macerator 200 may have at its distal end a distal hub 212 coupled to an inner macerator shaft 206 and at its proximal end a proximal hub 214 coupled to an outer macerator shaft 208. The plurality of maceration wires 197 may be attached to a macerator inner shaft 206, to the distal hub 212, or the proximal hub 214, or any combination thereof. The macerator inner shaft 206 may be slidably disposed over a guidewire shaft 150.

Various mechanisms of macerator actuation may be used, including: advancing the proximal hub 214 toward the distal hub 212 to cause the macerator 200 to expand from a delivery configuration; advancing the distal hub 212 toward the proximal hub 214 to cause the macerator 200 to expand from a delivery configuration; advancing both the proximal hub 214 and the distal hub 212 into a closer proximity with each other; or any combination thereof.

The dilator tip 120 and the corresponding distal end 116 of the capture basket 110 may be shaped so that as the dilator tip 120 and the capture basket 110 are advanced, they may more easily pass through a bodily lumen, especially a bodily lumen in which a clot is present. Moreover, as the dilator tip 120 and the capture basket 110 are advanced, further advancement may be limited by a bulb 162 at a distal end of a guidewire 160 acting as a wire stop, thereby limiting the travel of the dilator tip 120 and the capture basket 110. In some embodiments, the capture basket 110 acts as a filter in the event some clot particles escape while being trapped and/or macerated.

A single control wire 134c may be used so that as maceration occurs within the macerator 200, and a minimal set of the plurality of macerator wires 197 may interact with a minimal set of control wires. In some embodiments, none of the plurality of macerator wires 197 interact with any control wires. In other embodiments, every wire from the plurality of macerator wires 197 interacts with every control wire. The total number of interactions between the plurality of macerator wires 197 and control wires may be between those two extremes, with many embodiments minimizing the total number of interactions. As shown in FIG. 11, a single control wire 134c may be used and situated such that it does not interact with any of the plurality of macerator wires. In this way, the action of controlling the capture basket 110 may be independent of the process of maceration. In other embodiments, controlling the capture basket 110 may be dependent on the process of maceration and vice versa. In many embodiments, there may be one or more control wires.

Figure 12A:
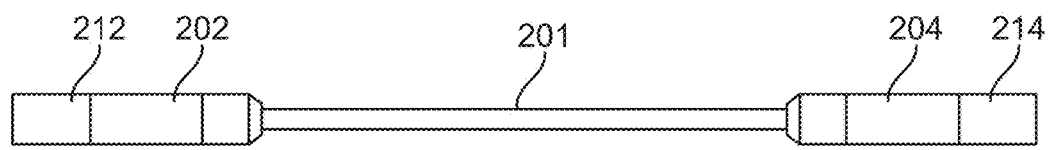
FIG. 12A shows a top view of a strut of a macerator element of a linear configuration, according to many embodiments.
Figure 12B:
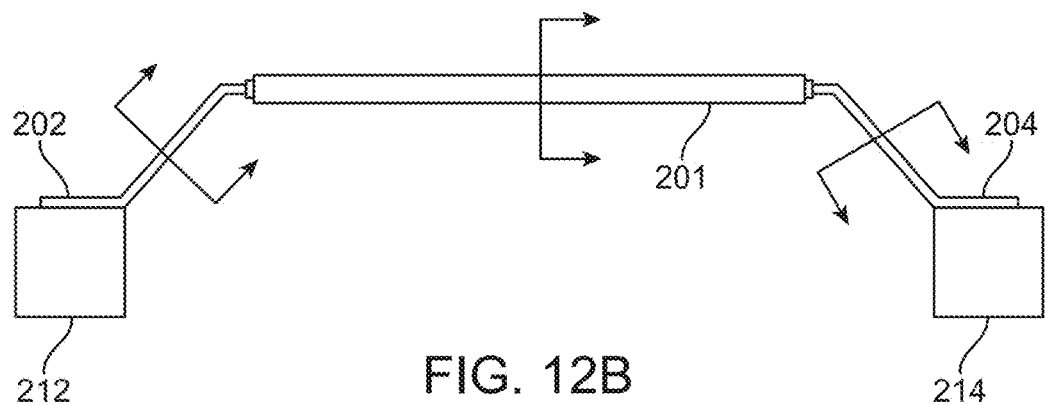
FIG. 12B shows a side view of a strut of a macerator element of a linear configuration, according to many embodiments.
Figure 12C:
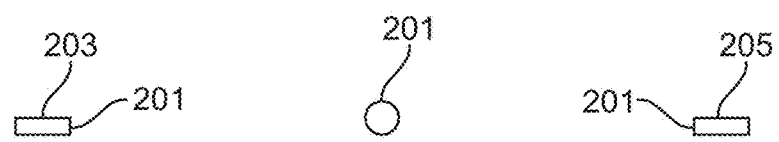
FIG. 12C shows various cross-sectional views of a strut of a macerator element of a linear configuration shown in FIG. 12B, according to many embodiments.

FIG. 12A-12C shows a top view, a side view, and a various cross-sectional views, respectively, of a macerator element 201 from a linear macerator 200 configuration, respectively. The macerator element 201 may comprise a distal portion 203 that terminates in a distal end 202 and a proximal portion 205 that terminates in a proximal end 204. The distal end 202 of the macerator element 201 may be attached to a distal hub 212 and the proximal end 204 may be attached to a proximal hub. Bringing the distal end 202 and the proximal end 204 closer to each other may actuate the macerator element 201. The macerator element 201 may have a varying cross-sectional profile across its length, as demonstrated in FIG. 12C. The cross-sectional profile may be generally circular, triangular, square, rectangular, trapezoidal, or any polygon, or any combination thereof.

Figure 13A:
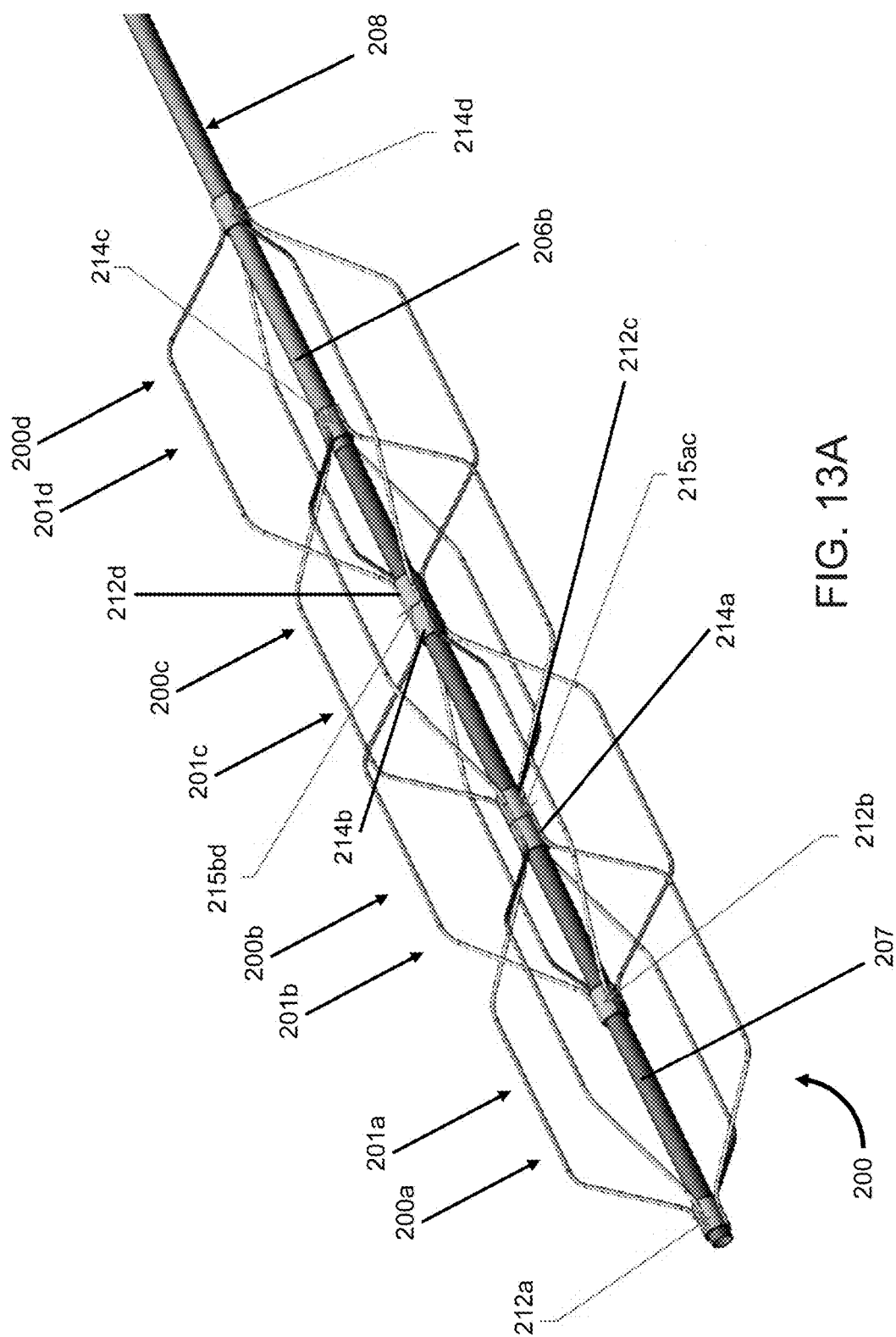
FIG. 13A shows a perspective view of a macerator structure for a clot extraction catheter having a combination of linear macerator elements, according to many embodiments.

FIGS. 13A-13C show a perspective view, a side view, and an end view, respectively, of a macerator 200 for a clot extraction catheter 100 having a plurality of macerator segments 200a, 200b, 200c, and 200d arranged in series. Each macerator segment 200a, 200b, 200c, 200d may have a distal end 212a, 212b, 212c, 212d and a proximal end 214a, 214b, 214c, 214d and a plurality of macerator elements 201a, 201b, 201c, 201d, which may comprise expandable wire cages. While FIGS. 13A-13C show four macerator segments 200a-200d whose plurality of macerator elements 201a-201d comprise linear segments, one of skill in the art will appreciated that any number of macerator segments with any type of macerator elements as described herein may be used. The macerator 200 may be disposed over an inner macerator shaft 206 and an outer macerator shaft 208. The distal ends 212a, 212b of the macerator segments 200a, 200b may be bound to the inner macerator shaft 206, the proximal ends 212c, 212d of the macerator segment 200c, 200d may be bound to the outer macerator shaft 208, and the proximal ends 214a, 214b of macerator segments 200a, 200b and the distal ends 212c, 212d of macerator segments 200c, 200d may slide over the inner macerator shaft 206. In the illustrated example, there are two hub-to-hub interfaces 215ac, 215bd where the distal ends 212c, 212d of the macerator segments 206c, 206d abut the proximal ends 214a, 214d of the macerator segments 206a, 206d. The hub-to-hub interface 215ac, 215bd may comprise a partially fixed engagement between hubs, a fully fixed engagement between hubs, or a non-fixed engagement between hub, or any combination thereof.

The macerator segments 200a-200d may comprise macerator elements 201a-201d that may be shaped to be linear, curvilinear, spiraled, helical, or any comparable profile. The macerator segments 200a-200d and/or the macerator elements 201a-201d may be made of a semi-elastic metal, such as nitinol. Many of the clot trap and/or macerator embodiments may comprise one or more macerator segments 200a-200d as described herein.

The inner macerator shaft 206 may be advanced distally to radially collapse the macerator 200, the plurality of macerator segments 200a-200d, and/or the plurality of macerator elements 201a-201d and/or may be retracted proximally to radially expand the macerator 200, the plurality of macerator segments 200a-200d, and/or the plurality of macerator elements 201a-201d. The outer macerator shaft 208 may be retracted proximally to radially collapse the macerator 200, the plurality of macerator segments 200a-200d, and/or the plurality of macerator elements 201a-201d and/or may be advanced distally to radially expand the macerator 200, the plurality of macerator segments 200a-200d, and/or the plurality of macerator elements 201a-201d. The macerator segments 200a-200d may be actuated simultaneously or may be independently actuatable.

FIGS. 14A-14C show a perspective view, a side view, and an end view, respectively, of a macerator 200 for a clot extraction catheter having a plurality of macerator segments 200a-200d having spiral or helical macerator elements 201a-201d. An increased number of macerator segments 200a-200d may increase flexibility of the macerator 200, for example, to reduce risk of trauma to curved vessels. The macerator 200, the macerator segments 200a-200d, and/or the macerator elements 201a-201d may be tapered in diameter along the length of the macerator 200, macerator segments 200a-200d, and/or macerator elements 201a-201d proximally to distally to conform to a natural tapering that comprise many vessels. Actuation of the individual macerator segments 200a-200d may take any form described herein.

FIG. 15A show a side view and an end view, respectively, of a macerator 200 for a clot extraction catheter having spiral or helical macerator elements 201a-201d disposed over an inner macerator shaft 206 and an outer macerator shaft 208. Each of the macerator elements 201a-201d may terminate at their distal end at a distal hub 212 and at their proximal end at a proximal hub 214 of the macerator 200. Each of the macerator elements 201a-201d may be configured in their spiral or helical profile to avoid contact with other macerator elements 201a-201d.

The spiral or helical macerator elements of many clot extraction catheter may aid in advancing the clot extraction catheter to a target site, may aid in navigating the macerator closer to a target site, and/or may aid in positioning the macerator to an optimal location with respect to a clot.

Figure 16A:
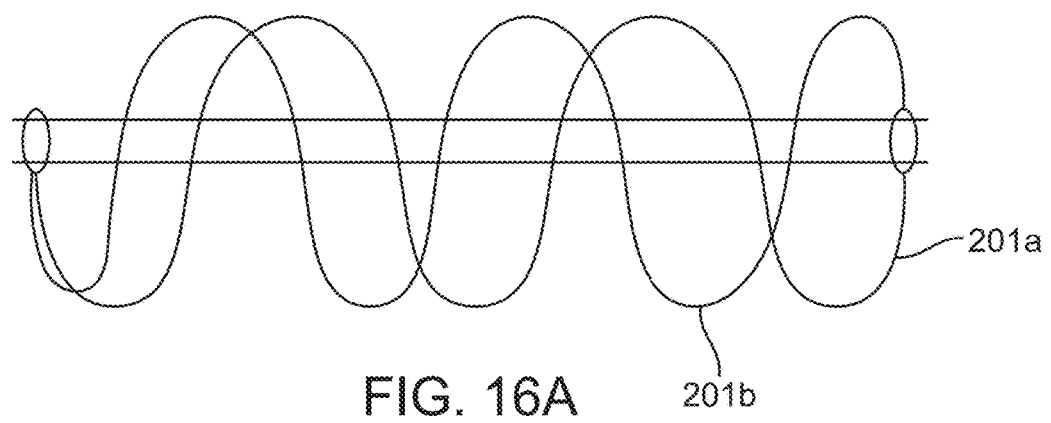
FIGS. 16A and 16B show various alternative patterns of spiral or helical macerator elements, according to many embodiments.
Figure 16B:
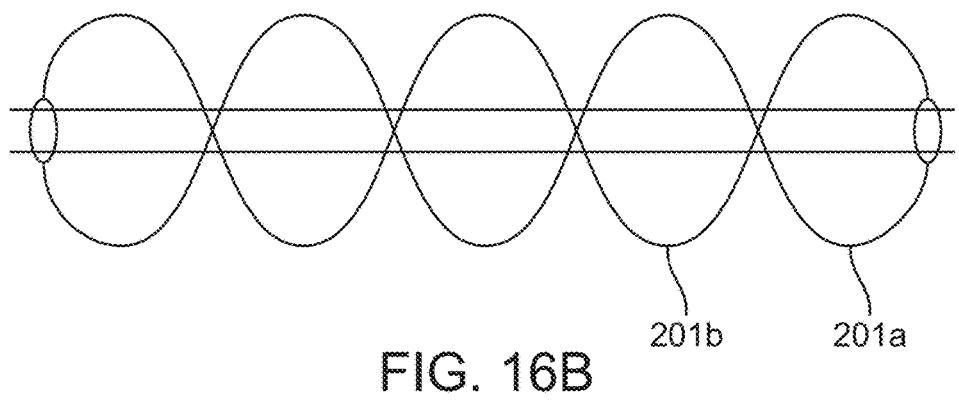

FIGS. 16A and 16B show various alternative patterns of spiral or helical macerator elements 201a, 201b. The macerator elements 201a, 201b may comprise one or more helices at least partially in phase with each other, as in FIG. 16A, or they may be at least partially out of phase, as in FIG. 16B, or any phase alignment combination between. The pitch of the helices may remain constant, vary randomly, or vary algorithmically, or any combination thereof, over the length of the macerator 200. Each helix of the one or more helices may comprise a circular helix, a conical helix, a cylindrical helix, a slant helix, or a helix whose edge profile can be described by the summation of any number of sine or cosine functions, or any combination thereof. Each helix of the one of more helices may be right-handed or left-handed.

Figure 17A:
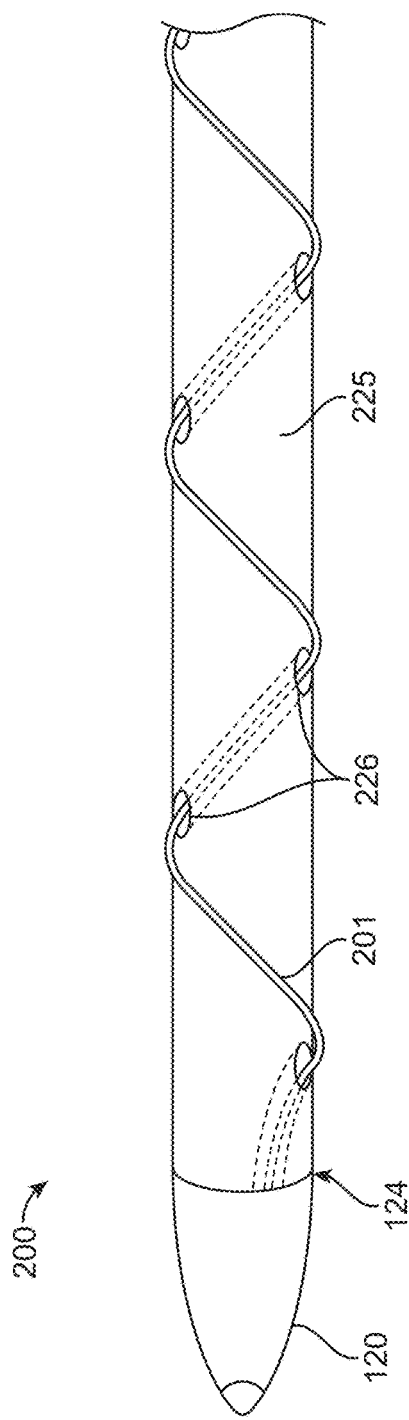
FIG. 17A shows a support structure for macerator elements with the macerator elements collapsed, according to many embodiments.
Figure 17B:
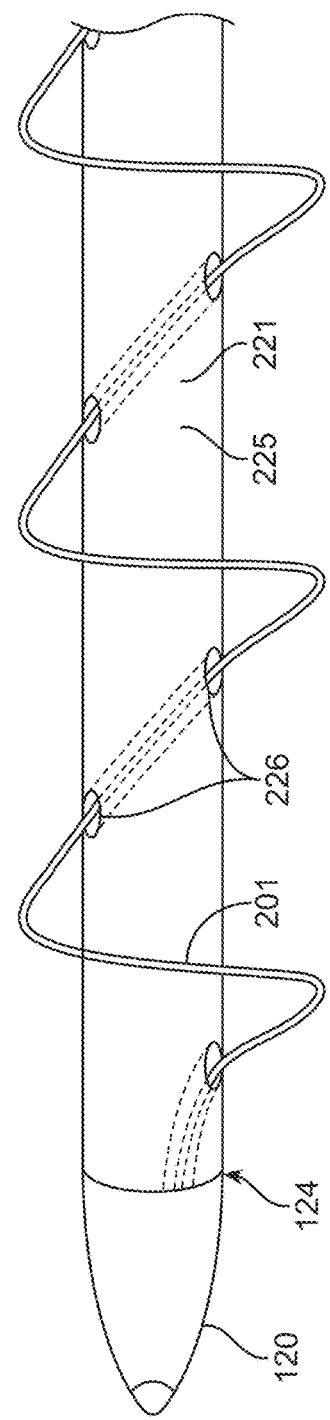
FIG. 17B shows the support structure for macerator elements of FIG. 17A with the macerator elements expanded, according to many embodiments.

FIGS. 17A and 17B show a support structure 220 for a macerator 200 with a macerator element 201 contracted and extended, respectively. The support structure 220 may have a distal end 222 and a proximal end 224, the distal end 222 of the support structure 220 coupled to a proximal end 124 of a dilator tip 120, and may be further comprised of conduits 225 configured to slidably engage the macerator element 201. Conduit holes 226 may allow the macerator element 201 to enter into a conduit 225 or to exit from a conduit 225. In the contracted state, portions of the macerator element 201 may reside either within a conduit 225 or reside on a surface 221, either an inner surface or an outer surface, of the support structure 220. In the expanded state, portions of the macerator element 201 may reside either within a conduit 225 or are expanded away from the support structure surface 221. The addition of the conduits may have the benefit of preventing the macerator element from buckling during actuation of the macerator 200.

Though referenced here using a singular macerator element 201, it should be noted that any number of macerator elements may be used. Conduits may be configured to allow one or more macerator elements.

Figure 18A:
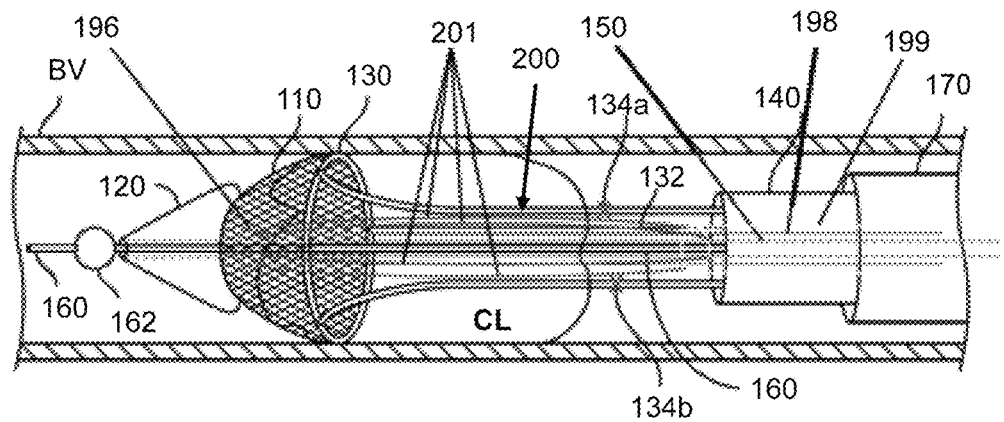
FIGS. 18A, 18B, and 18C show cross-sectional side views of an exemplary clot extraction catheter extended in a blood vessel and having its wire net extended, according to many embodiments.
Figure 18B:
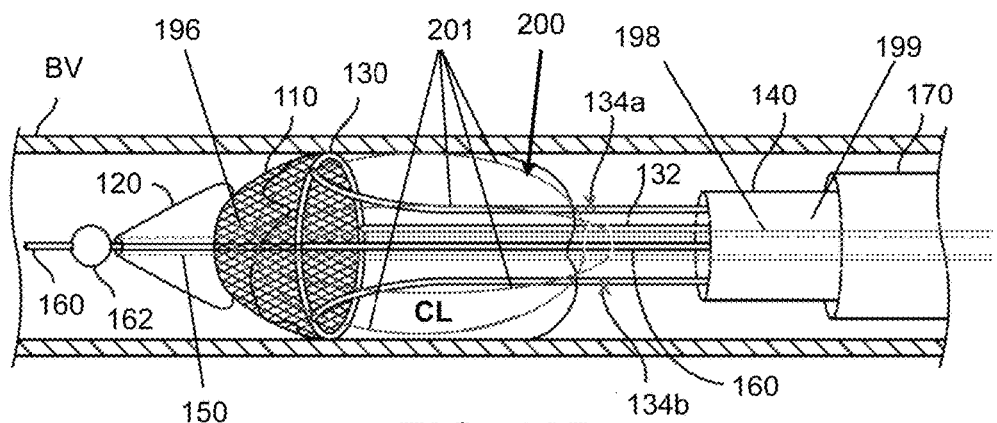
Figure 18C:
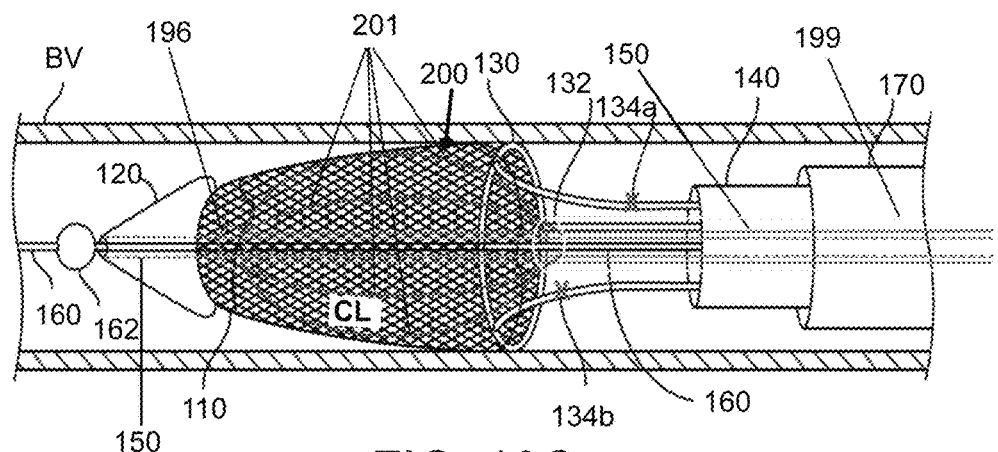

FIGS. 18A-18C show cross-sectional side views of an exemplary clot extraction catheter 100 having a macerator 200. The macerator 200 may be mounted to macerator shaft 198 and macerator sheath 199 within the inner sheath 140 and may be slidably disposed over a guidewire channel 150. The control wires control wires 132, 134a, and 134b of net 110 may surround macerator 200. The macerator 200 may be coupled at its proximal end to macerator sheath 199, and may be coupled at its distal end to the distal end 196 of macerator shaft 198.

FIG. 18A shows the net 110 extended and axially collapsed and macerator 200 collapsed, with the net 110 disposed distal to clot CL and macerator 200 disposed adjacent clot CL.

FIG. 18B shows the macerator 200 being expanded. Macerator 200 may be expanded by advancing distally macerator sheath 199, or by methods previously described herein. When expanded, macerator 200 may expand into clot CL and thereby may break up clot CL. When expanded, the macerator 200 may urge the control wires 132, 134a, and 134b of net 110 laterally outward, or the macerator 200 may expand around control wires 132, 134a, and 134b leaving the control wires in place, or may urge the control wires 132, 134a, and 134b in any position therebetween.

FIG. 18C shows the net 110 being retracted over macerator 200 after the macerator 200 has been expanded into clot CL. Net 110 may be retracted as previously described herein.

Figure 19A:
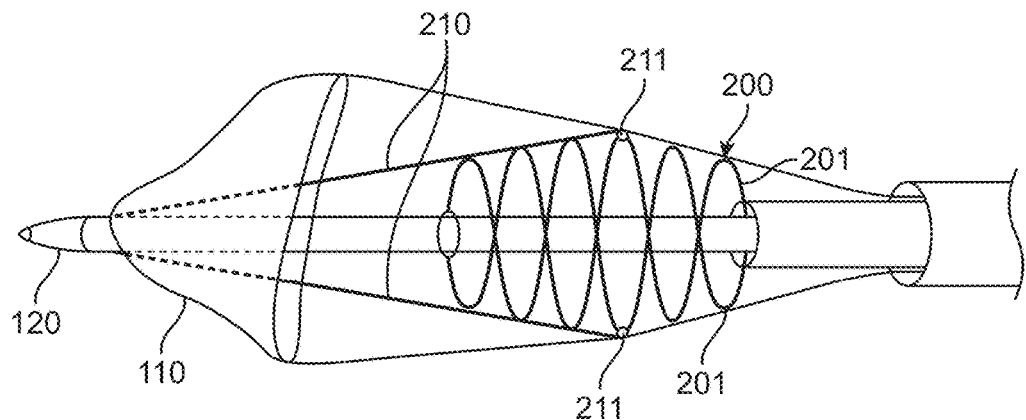
FIGS. 19A and 19B show side views of an exemplary clot extraction catheter having a plurality of guide wires attached to macerator elements used to guide the net over the macerator elements.
Figure 19B:
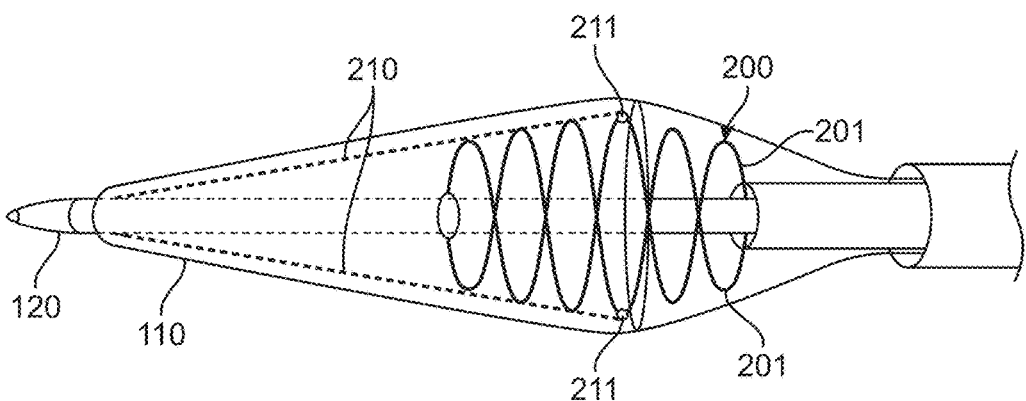

FIGS. 19A and 19B show a clot extraction catheter 100 which comprises a macerator 200 having one or more macerator elements 201. One or more guide wires 210 may be attached to the one or more macerator elements 201. The one or more guide wires 210 may be attached distally to the dilator tip 120 as shown, or may be attached to the proximal end of macerator 200, or anywhere therebetween. The one or more guide wires 210 may be proximally attached to any number of the one or more macerator elements 201 of macerator 200 and at any location 211 of the one or more macerator elements 201. Further, in embodiments with one or more macerator segments (not shown), the guide wires 201 can attached to any number of macerator segments and at any location of the one or more macerator segments. As shown is FIG. 19A, the net 110 is extended and axially collapsed and located distal to the macerator 200 in its expanded configuration with attached guide wires 210.

Upon retraction and axial extension of net 110 as shown in FIG. 19B, the one or more guide wires 210 function as guides to allow the net 110 to pull over the expanded macerator 200. Any number of guide wires 210 may be used for this purpose. The one or more guide wires 210 can also function to allow net 110 to pull over macerator 200 in its collapsed configuration, or macerator 200 in between its fully collapsed and expanded configuration. The one or more guide wires 210 may also function to prevent buckling of macerator 200 when transitioned from its collapsed and expanded configurations.

FIG. 20A shows a clot extraction catheter 100 having macerator 200 in their collapsed configuration and positioned adjacent a clot CL, with the capture basket 100 located distal to the macerator 200 and clot CL. As shown in FIG. 20B, in this exemplary embodiment the macerator 200 can be expanded into the clot CL by advancing distally the outer macerator shaft 208 attached to a proximal end 209 of the macerator 200. The outer macerator shaft 204 may be pulled proximally and advanced distally any number of times to cause the macerator 200 to be collapsed and expanded, respectively, so as to break up the clot CL. A distal end 207 of the macerator 200 may be connected to an inner macerator shaft 206.

FIGS. 21A-21C show an exemplary clot extraction catheter 100 with a macerator 200 that may be transitioned from a collapsed configuration (as seen in FIG. 21A) to an expanded configuration (as seen in FIG. 21B) to a twisted configuration (as seen in FIG. 21C). FIG. 21A shows the exemplary clot extraction catheter 100 with a macerator 200 in an initially collapsed configuration, with a capture basket 110 located distal to the macerator 200. As shown in FIG. 21B, advancing an outer macerator shaft 208 attached to a proximal end of the macerator 209 may cause the macerator 200 to expand. As shown in FIG. 21C, twisting the outer macerator shaft 208 may cause the macerator 200 to assume a twisted configuration. Alternatively or in combination, an inner macerator shaft 206 may be twisted to cause the macerator 200 to assume a twisted configuration. The outer macerator shaft 208 or the inner macerator shaft 206 may be independently twistable or may twist together in the same direction or may twist together in opposite directions, or any combination thereof. The outer macerator shaft 208 or the inner macerator shaft 206 may be twisted either clockwise or counterclockwise any number of times to cause the macerator 200 to assume a desired clockwise or counterclockwise twisted configuration, respectively. Such translational and/or rotational manipulation of the outer macerator shaft 208 or the inner macerator shaft 206 may aid in breaking up a clot. Furthermore, any combination of translational and rotational manipulations of the outer macerator shaft 208 or the inner macerator shaft 206 may be performed any number of times to aid in breaking up a clot. For example, the inner macerator shaft 206 may be advanced distally and retracted proximally while the outer macerator shaft 208 is twisted first in a clockwise direction and then in a counterclockwise direction. Such an example is not intended to be limiting and is merely meant as an illustrative case.

Referring to FIGS. 22A and 22B, an exemplary method for thrombolysis and aspiration using a clot capture device 100 as described herein is described.

Step 1: After a capture basket 110 is delivered distal to a clot CL, and more specifically in this case, a thrombus, in a telescoped or collapsed state from an inner tubular sheath 140, a macerator 200 (also referred herein throughout as a clot trap) may become engaged with the thrombus CL by further retracting the inner tubular sheath 140. For the sake of illustrative clarity, the trap/macerator 200 has been omitted from the figure; however, one of skill in the art will appreciate its intended effects from previous figures demonstrating its function and structure.

Step 2: The trap/macerator 200 may be expanded within the thrombus CL by pushing and/or pulling on an inner macerator shaft 206 or an outer macerator shaft 208 and/or by manually rotating the inner macerator shaft 206 or the outer macerator shaft 208 to engage, surround, and macerate the thrombus CL.

Step 3: In some cases, in addition to mechanical removal of thrombus CL within the capture basket 110, pharmaco-mechanical and/or other forms of fragmentation (see step 7) of the thrombus CL may be necessary.

Step 4: After the capture basket 110 is pulled over and completely covers the clot CL and the trap/macerator 200, the trap/macerator 200 may be collapsed, expanded and rotated multiple times as desired to continue to fragment and macerate the thrombus CL.

Step 5: The one piece or multi segmented trap/macerator 200 may be removed from or advanced into the thrombus CL filled capture basket 110 inside the tubular inner sheath 140 and over the guidewire shaft 150 by:

(a) first collapsing one or more macerator elements 201 and/or the trap/macerator 200 completely and locking an inner macerator shaft 206 and an outer macerator shaft 208 with respect to each other;

(b) the trap/macerator 200 may also be rotated and or translated in any number of directions for the respective motions to free it from or to help further macerate the clot CL in the capture basket 110 over the guidewire shaft 150; and (c) the inner tubular shaft 140 may be advanced to or partially over the capture basket rim 130 to slightly close the rim 130 to allow the clot to be stripped at the capture basket rim 130 from the trap/macerator 200 while withdrawing.

Step 6: In some embodiments, an expandable element 191 (such as a balloon) may be inflated at a distal tip of a pusher sheath 195 to prevent the thrombus CL from being pulled out within or without the collapsed trap/macerator 200 while it is being pulled into the inner tubular sheath 140.

Step 7: After the trap/macerator 200 is withdrawn, to reduce the clot burden to be removed within the net, known devices with pharmacological, ultrasonic, mechanical, electrical, thermal, and/or other sources of energy may be introduced into the net through either the inner tubular sheath 140 over the guidewire shaft tube or the outer tubular sheath 170 and activated and applied to the trapped clot CL to further fragment it into particles small enough to be released through interstices of the capture basket 110 and/or to be aspirated from the capture basket 110.

Step 8: While any such maceration device, including the trap/macerator 200 is in active use, the rim 130 of the capture basket 110 may be closed as previously described above (see at least step 5(c)) to prevent distal embolization of fragmented thrombus CL by withdrawing it into the inner tubular sheath 140 or advancing the inner tubular sheath 140 over the capture basket rim 130.

Step 9: In some embodiments of such a pharmaco-mechanical device, a multi side hole thrombolysis catheter 240 which has an end hole that may be tapered toward the guidewire shaft tube 150 may be introduced toward and into the clot CL filled capture basket 110 coaxially within a thin walled aspiration sheath 230. The taper of the thrombolysis catheter 240 may allow the thrombolysis catheter 240 to function as a tip-occluded multi-side hole lysis catheter as well as to serve as a coaxial dilator introducer for the aspiration sheath 230.

Step 10: The multi side hole thrombolysis catheter 240 may be advanced partially towards or fully to a distal end 112 of the capture basket 110 while a distal end 232 of the aspiration sheath 240 may remain outside of and proximal to the capture basket 110.

Step 11: Following pharmaco-mechanical thrombolysis, the aspiration sheath 230 may be advanced to the distal end 112 of the capture basket 110 over the thrombolysis catheter 240 and the thrombolysis catheter 240 may then be removed.

Step 12: The aspiration sheath 230 may have a sidearm to allow for aspiration of fragmented thrombus CL. Aspiration thrombectomy may be performed, for example, by applying suction manually or with a mechanical device to a syringe attached to the sidearm of the aspiration sheath 230.

Step 13: Thrombolysis or aspiration may be performed sequentially (as in step 9), but each may be performed individually without the other.

The above steps may comprise one or more sub-steps. One or more of the steps and/or sub-steps may be omitted or repeated as beneficial for the treatment. The steps and/or sub-steps may be performed in different orders as beneficial for the treatment.

Figure 23A:
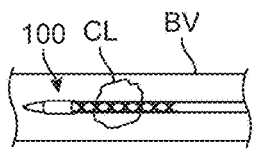
FIGS. 23A, 23B, 23C, and 23D show various views of a clot extraction catheter being used to capture a clot after piercing through a clot, according to many embodiments.
Figure 23B:
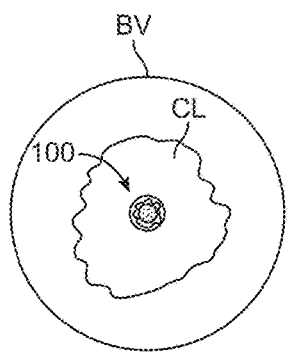
Figure 23C:
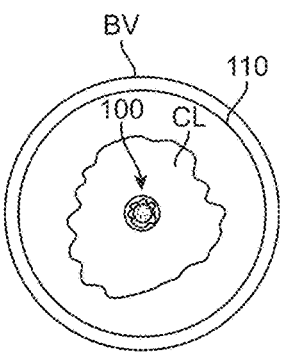
Figure 23D:
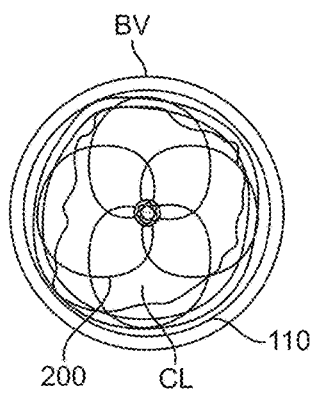

FIGS. 23A-23D show various views of an exemplary clot extraction catheter 100 in a blood vessel BV being used to capture a clot CL after piercing through a portion of the clot CL. FIG. 23A shows a side view of the clot extraction catheter 100 after it has been advanced distally and pierced through a portion of the clot CL while in its fully collapsed configuration. FIG. 23B shows an end view of the clot extraction catheter 100 corresponding to FIG. 23A. FIG. 23C shows and end view of the clot extraction catheter 100 with its capture basket 110 expanded distal to the clot and a macerator 200 in a collapsed configuration. FIG. 23D shows an end view of the clot extraction catheter 100 with its capture basket 110 expanded distal to the clot CL with the macerator 200 in an expanded configuration. FIGS. 23A-23D demonstrate the clot extraction catheter 100 may pass through some portion of the clot CL.

Figure 24A:
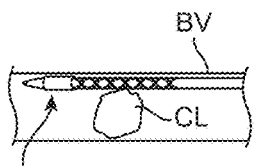
FIGS. 24A, 24B, 24C, and 24D show various views of a clot extraction catheter being used to capture a clot after passing by a clot, according to many embodiments.
Figure 24B:
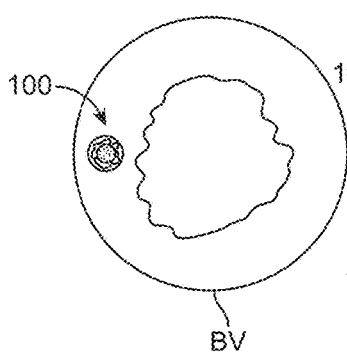
Figure 24C:
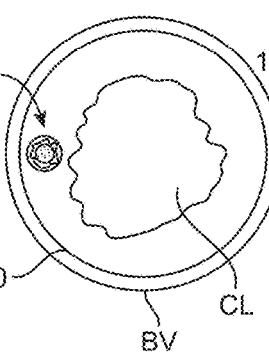
Figure 24D:
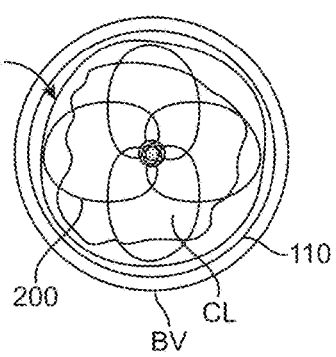

FIGS. 24A-24D show various views of an exemplary clot extraction catheter 100 in a blood vessel BV being used to capture a clot CL after being advanced distally between the clot CL and clot extraction catheter 100. FIG. 24A shows a side view of the clot extraction catheter 100 after it has been advanced distally between the clot CL while in its collapsed configuration. FIG. 24B shows an end view of the clot extraction catheter 100 corresponding to FIG. 24A. FIG. 24C shows and end view of the clot extraction catheter 100 with its capture basket 110 expanded distal to the clot CL and with a macerator 200 in a collapsed configuration FIG. 24D shows an end view of the clot extraction catheter 100 with its capture basket 110 expanded distal to the clot with the macerator 200 in an expanded configuration. As further shown in FIG. 24D, by expanding the macerator 200, the clot extraction catheter 100 can be forced to engage the clot CL. FIGS. 24A-24D demonstrate the clot extraction catheter 100 may pass along some portion of the blood vessel BV without passing through any portion of the clot CL, but rather pass along a side of the clot CL.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the disclosure. It should be understood that various alternatives to the embodiments of the disclosure described herein may be employed in practicing the invention. It is intended that the following claims define the scope of the invention and that methods and structures within the scope of these claims and their equivalents be covered thereby.

What is claimed is:

1. A clot extraction catheter comprising:
   an expandable tubular mesh having a distal end and a proximal end, the tubular mesh having an expanded configuration and a constrained configuration;
   a self-expanding rim attached to the proximal end of the expandable tubular mesh, the self-expanding rim having an unconstrained diameter which is greater than a width of the proximal end of a tapered tip;
   at least one control wire attached to the self-expanding rim and disposed radially over a guidewire channel;
   an inner sheath advancable over the at least one control wire to constrain at least a portion of the self-expanding rim and at least a portion of the tubular mesh within a lumen of the inner sheath; and
   at least one clot maceration wire advancable from the inner sheath and radially expandable to facilitate clot maceration,
   wherein the at least one control wire is configured to be manipulated to control an angle of the self-expanding rim relative to an axis of the inner sheath when the self-expanding rim is unconstrained.

2. The clot extraction catheter as in claim 1, further comprising an outer sheath advancable over the inner sheath and the guidewire channel.

3. The clot extraction catheter as in claim 2, further comprising an expandable element.

4. The clot extraction catheter as in claim 3, wherein the expandable element is mounted on a distal end of the outer sheath.

5. The clot extraction catheter as in claim 3, wherein the expandable element is mounted on a pusher sheath being translatable relative to one or more of the inner or outer sheaths.

6. The clot extraction catheter as in claim 1, further comprising the guidewire channel disposed within the expandable tubular mesh and extending to the tapered tip, the guidewire channel having a guidewire lumen configured for a guidewire to be threaded therethrough.

7. The clot extraction catheter as in claim 6, wherein the plurality of control wires comprises at least three control wires which comprises a main wire translatable proximally and distally and two chord wires translatable proximally and distally independently from the main wire to control the angle of the self-expanding rim relative to the axis of the shaft when the self-expanding rim is unconstrained.

8. The clot extraction catheter as in claim 1, wherein the at least one control wire comprises a plurality of control wires.

9. The clot extraction catheter as in claim 1, wherein the at least one clot maceration wire comprises a plurality of clot maceration wires.

10. The clot extraction catheter as in claim 1, wherein the at least one clot maceration wire has one or more of a helical, spiral, sinusoidal, zig-zag, bracketed, curved, linear, tangled, or curvilinear shape.

11. The clot extraction catheter as in claim 1, wherein the proximal end of the expandable tubular mesh is open.

12. The clot extraction catheter as in claim 1, wherein the self-expanding ring and the at least one clot maceration wire are axially translatable independently from one another.

13. A method for extracting a clot from a bodily vessel or cavity, the method comprising:
    advancing a clot extraction catheter over a guidewire to position a distal end of a tapered tip of the clot extraction catheter in a lumen of the bodily vessel or cavity proximal of a clot, the guidewire being disposed within a guidewire channel of the clot extraction catheter;
    advancing the tapered tip past the clot such that a proximal end of the tapered tip is distal of the clot;
    opening a rim coupled to a proximal end of a tubular mesh of the clot extraction catheter to open the proximal end of the tubular mesh;
    retracting the tubular mesh proximally to capture the clot within the tubular mesh;
    adjusting an angle of the opened rim relative to a sheath of the clot extraction catheter before or during retracting of the tubular mesh to capture the clot contacting the clot with at least one clot maceration wire of the clot extraction catheter as the tubular mesh is retracted;
    closing the rim to close the proximal end of the tubular mesh and enclose the captured clot within the tubular mesh; and
    removing the clot extraction catheter from the lumen of the bodily vessel or cavity.

14. The method for extracting a clot as in claim 13, wherein contacting the clot with the at least one clot maceration wire comprises macerating the clot with the at least one maceration wire.

15. The method for extracting a clot as in claim 14, wherein macerating the clot comprises one or more of axially translating or rotating the at least one clot maceration wire contacting the clot.

16. The method for extracting a clot as in claim 13, wherein the at least one clot maceration wire comprises a plurality of maceration wires.

17. The method for extracting a clot as in claim 13, further comprising radially expanding the at least one clot maceration wire.

18. The method for extracting a clot as in claim 13, wherein the blood vessel is selected from the group comprising a vein, an artery, the aorta, a pulmonary artery, a vena cava, an inferior vena cava (IVC), a superior vena cava (SVC), an internal jugular vein, an external jugular vein, a subclavian vein, a hepatic vein, a renal vein, an iliac vein, a common iliac vein, an internal iliac vein, an external iliac vein, a femoral vein, and a peripheral vein.

* * * * *